(12) United States Patent
Shmulewitz et al.

(10) Patent No.: US 7,083,588 B1
(45) Date of Patent: Aug. 1, 2006

(54) APPARATUS FOR PROVIDING CORONARY RETROPERFUSION AND METHODS OF USE

(75) Inventors: Ascher Shmulewitz, Seattle, WA (US);
John Burton, Minnetonka, MN (US);
Robert S. Bley, Menlo Park, CA (US);
Roy Singfatt Chin, Fremont, CA (US);
Ronald C. Brown, Santa Cruz, CA (US); Robert L. Wilcox, Bothell, WA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 0 days.

(21) Appl. No.: 09/320,172

(22) Filed: May 26, 1999

Related U.S. Application Data

(63) Continuation-in-part of application No. 09/183,752, filed on Oct. 30, 1998, now abandoned, which is a continuation-in-part of application No. 09/084,513, filed on May 26, 1998, now abandoned.

(51) Int. Cl.
*A61M 5/00* (2006.01)
(52) U.S. Cl. ............................................. 604/8
(58) Field of Classification Search ............ 604/4, 604/8, 9; 623/3, 12.1; 600/16, 504
See application file for complete search history.

(56) References Cited

U.S. PATENT DOCUMENTS

| | | | | |
|---|---|---|---|---|
| 4,662,355 A | * | 5/1987 | Pieronne et al. | 600/17 |
| 4,995,857 A | * | 2/1991 | Arnold | 600/16 |
| 5,135,467 A | * | 8/1992 | Citron | 600/16 |
| 5,662,711 A | * | 9/1997 | Douglas | 604/9 |
| 5,965,089 A | * | 10/1999 | Jarvik et al. | 422/44 |

* cited by examiner

*Primary Examiner*—Manuel Mendez
(74) *Attorney, Agent, or Firm*—Stout, Uxa, Buyan & Mullins LLP

(57) ABSTRACT

Apparatus and methods for perfusing ischemic myocardium, and optionally, for reducing the load on a patient's left ventricle, are provided using a inlet conduit having an inlet end configured for insertion into an oxygenated blood source, including without limitation, the left atrium, left ventricle, aorta, pulmonary vein, subclavian artery, brachiocephalic artery, radial artery or femoral artery, coupled to an outlet conduit having an outlet end configured for insertion into the coronary venous vasculature via the coronary ostium. The inlet conduit may include a stylet or elastomeric sleeve that facilitates placement, while the outlet conduit may include a valve for limiting a peak pressure attained in the coronary venous system. A motor-driven or hydraulically-actuated pump optionally may be coupled in the flow path, and control circuitry provided to control the pump with a user selected duty cycle.

14 Claims, 12 Drawing Sheets

APPARATUS FOR PROVIDING CORONARY RETROPERFUSION AND METHODS OF USE

This application is a continuation-in-part of application Ser. No.: 09/183,752, filed Oct. 30, 1998. Now ABN which is a continuation-in-part of application Ser. No. 09/084,513, filed May 26, 1998 Now ABN.

FIELD OF THE INVENTION

The present invention relates generally to treatment and/or diagnosis of ischemic heart disease prior to, during, or after a corrective procedure, such as bypass grafting, heart replacement or angioplasty, and involves perfusing the myocardium with oxygenated blood.

BACKGROUND OF THE INVENTION

Each year worldwide several millions of patients undergo cardiac bypass surgery, during which stenosed and atherosclerotic cardiac vessels are replaced with native veins or arteries harvested elsewhere from the body.

A first step in treating or correcting cardiac disease, such as coronary artery disease, is to determine which portions of the heart are most likely to benefit from revascularization. In this manner, the clinician is able to assess the functioning of the myocardium, the location of infarcted or distressed areas, and select an appropriate treatment plan, e.g., an open-chest surgical procedure, "keyhole" coronary artery bypass grafting ("CABG") or angioplasty. Several methods of determining cardiac functioning are described, for example, in Udelson, "Steps Forward in the Assessment of Myocardial Viability in Left Ventricular Dysfunction," Circulation, 97:833–838 (1998). It would therefore be desirable to provide methods and apparatus that enhance a clinician's ability to better assess left ventricular dysfunction.

Patients often experience irreversible damage to ischemic myocardium while awaiting corrective therapy or surgery. It would therefore be desirable to provide apparatus and methods for preserving the myocardium of patients awaiting a corrective procedure.

A number of techniques have been developed to preserve the myocardium during corrective procedures, such as angioplasty and bypass procedures, that involve perfusing the heart using the coronary venous system. For cardiac surgery, a patient's heart is typically stopped, and the patient is placed on a cardiopulmonary bypass machine. Hypothermia is induced and maintained in the heart throughout the bypass operation to reduce necrosis of the myocardium caused by oxygen starvation.

Coronary retroperfusion also may be used to preserve ischemic myocardium, as described in Kuraoka et al., "Antegrade or Retrograde Blood Cardioplegic Method: Comparison of Post-Surgical Right Ventricular Function and Conduction Disturbances," Japanese J. Thoracic Surg., 48(5): 383–386 (1995); Ihnken et al., in "Simultaneous Arterial and Coronary Sinus Cardioplegic Perfusion, an Experimental and Clinical Study," Thoracic and Cardiovascular Surgeon, 42(6):141–147 (1994); and Lincoff et al., "Percutaneous Support Devices for High Risk or Complicated Coronary Angioplasty," J. Am. Coll. Cardiol., 17(3):770–780 (1991)).

Retrograde blood flow through the coronary venous system may be augmented by coronary ostial occlusion, as described in Rudis et al. in "Coronary Sinus Ostial Occlusion During Retrograde Delivery of Cardioplegic Solution Significantly Improves Cardioplegic Distribution and Efficiency," J. Thoracic &Cardiovasc. Surg., 109(5):941–946 (1995). In this case, blood flows retrograde to the myocardium and drainage is through the lymphatic system and the Thebesian veins.

Aldea, et al., in "Salvage of Ischemic Myocardium With Simplified and Even Delayed Coronary Sinus Retroperfusion," Ann. Thorac. Sure., 62:9–15 (1996), describe three techniques for preserving ischemic myocardium during a simulated bypass operation. The first method, referred to as pressure-controlled intermittent coronary sinus retroperfusion ("PICSO") involves placing a balloon in the coronary sinus, which is periodically inflated and deflated. When the balloon is inflated, blood draining into the coronary sinus is passively redirected in a retrograde manner through the coronary venous system, thereby perfusing the myocardium.

A second method described in the Aldea article is synchronized retroperfusion ("SRP"). In SRP, a balloon is placed in the coronary sinus, and in synchrony with balloon inflation, oxygenated blood is pumped into the coronary sinus so that it flows in a retrograde manner. The balloon is inflated, and blood injected into the coronary sinus, only during diastole. During systole, the balloon is deflated and blood flow into the coronary sinus ceases.

A third method, described in the Aldea article as simplified retroperfusion ("SR"), is similar to SRP, but no balloon is placed in the coronary sinus. Instead, a pump is used to continuously inject blood into the coronary sinus. Apparatus suitable for use with the foregoing methods is described in U.S. Pat. No. 5,597,377 to Aldea.

The foregoing methods generally may be used as adjuncts to hypothermia to preserve the myocardium during stenting or high-risk percutaneous transluminal coronary angioplasty (PTCA). Surgical techniques, however, such as developed by Cardio Thoracic Systems, of Menlo Park, Calif., also enable coronary artery bypass grafting ("CABG") to be performed on a beating heart. In accordance with those methods, the heart is not stopped, but instead the bypass surgery is performed while the heart is beating. It therefore would be desirable to provide simpler methods and apparatus that enable the clinician to preserve the myocardium during beating heart cardiac surgery, PTCA or stenting.

In addition, once the bypass operation is completed, the heart is revived and blood flow through the heart is restored to normal. In some cases, however, there may be some difficulty in weaning the patient from the cardiopulmonary bypass machine. In particular, the heart can become overexerted when attempting to restore flow in the arterial system. In these situations, an intra aortic balloon pump ("IABP") may be used to lower the pressure encountered by the left ventricle during systole.

The intra-aortic balloon pump generally comprises a balloon catheter which is placed in the ascending aorta or aortic arch, and which is cyclically inflated and deflated in synchrony with the heart. In particular, the balloon is inflated during cardiac diastole, so that blood in the aorta is urged into the descending aorta. The balloon is then deflated in anticipation of systole, and reduces the pressure against which the left ventricle ejects blood during contraction.

In "Enhanced Preservation of Acutely Ischemic Myocardium With Transseptal Left Ventricular Assist," Ann. Thor. Sure. 57:570–575 (1994), Fonger et al., describe an experimental left ventricular assist device ("LVAD") for use in weaning a cardiac bypass patient from a cardiopulmonary bypass machine. The device comprises a pump having an inlet catheter disposed in the left atrium via a femoral vein and an outlet catheter located in a femoral artery. The article describes that the LVAD device reduces the load on the left ventricle by draining a portion of the blood from the left atrium into the femoral artery.

It also would be desirable to provide apparatus and methods that assist the left ventricle, by reducing the volume of blood pumped by, and thus, the exertion of, the left ventricle in patients awaiting, or who have completed, cardiac bypass surgery.

SUMMARY OF THE INVENTION

In view of the foregoing, it is an object of the present invention to provide methods and apparatus that enhance a clinician's ability to better assess left ventricular dysfunction by providing coronary retroperfusion.

It is another object of this invention to provide apparatus and methods for preserving ischemic myocardium of patients awaiting corrective procedures.

It also is an object of the present invention to provide methods and apparatus that enable the clinician to preserve the myocardium during beating heart cardiac surgery, PTCA and stenting.

It is a further object of this invention to provide apparatus and methods for providing retrograde short-term perfusion of the myocardium prior to, during, or after a corrective procedure.

It is a further object of this invention to provide apparatus and methods that assist the left ventricle, by reducing the volume of blood pumped by, and thus, the exertion of, the left ventricle in patients awaiting, undergoing, or who have completed, cardiac bypass surgery.

These and other objects of the present invention are achieved by providing apparatus and methods for perfusing the myocardium via the coronary venous vasculature using blood from an oxygenated blood supply, including without limitation, the left atrium, left ventricle, aorta, pulmonary vein, subclavian artery, brachiocephalic artery, radial artery or femoral artery (hereinafter, referred to as "a source of oxygenated blood"). Apparatus constructed in accordance with the present invention comprises an inlet conduit having an inlet end configured for insertion into a source of oxygenated blood, which is coupled to an outlet conduit having an outlet end configured for insertion into the coronary venous vasculature via the coronary ostium. The apparatus may be used for diagnosis of cardiac dysfunction, or prior to, during or after a corrective procedure.

In a first embodiment, the inlet conduit and outlet conduits are individually inserted and then coupled together, or comprise portions of a unitary device, and rely upon the pressure differential between the arterial blood source and the coronary venous vasculature to cause the blood to perfuse the myocardium in retrograde fashion. In other embodiments, the apparatus may employ a mechanically actuated or motor-driven pump to enhance retrograde perfusion. Therapeutic agents, such as drugs, bioactive agents or angiogenic growth factors, or cooled saline may be added to the blood passing through the circuit. Alternatively, external portions of the inlet and/or outlet conduit or both may be disposed in a cooling bath.

The inlet conduit preferably comprises a catheter and may be inserted either intraoperatively on a removable stylet or retractable cannula, or percutaneously using a guidewire extending through a proximal end of the catheter or a side port. The outlet conduit preferably comprises a catheter including means for retaining the end of the catheter in the coronary vasculature, such as soft elastomeric barbs, a balloon or a combination thereof, and may partially or fully occlude the coronary ostium or a localized portion of the venous vasculature. The outlet conduit further may include a valve that permits excess blood to be vented to the right atrium when pressure in the outlet conduit exceeds a predetermined limit. Optionally, one or more of the inlet and outlet conduits, may include a sensor element that provides signals used to compute flow-related parameters for blood passing through the circuit.

Where motor-driven pump is employed, it preferably is operated with a duty cycle designed to control a parameter related to the pressure in the coronary venous system, so as to reduce the potential for edema of the venous system. Control circuitry optionally may be provided to activate the pump with a user selected duty cycle to reduce exertion of the left ventricle by draining blood from the left atrium or left ventricle and injecting that blood into the coronary venous system to provide retrograde perfusion.

Methods of placing and operating apparatus constructed in accordance with the present invention are also provided. In addition, methods for placing flow sensors and measuring flow-related parameters also are provided. Methods of operating the inventive apparatus also are provided for postoperative weaning of the patient from cardiac bypass.

BRIEF DESCRIPTION OF THE DRAWINGS

Further features of the invention, its nature and various advantages will be more apparent from the accompanying drawings and the following detailed description of the invention, in which:

FIGS. 4A, 4B and 4C are detailed sectional views of the distal end of the inlet conduit of FIG. 3, while

FIGS. 6A and 6B are detailed sectional views of the distal end of the inlet conduit of FIG. 5, while

DETAILED DESCRIPTION OF THE INVENTION

The present invention relates generally to methods and apparatus for diagnosing cardiac dysfunction and for providing short-term (e.g., from a few minutes to several weeks) transvenous myocardial perfusion for patients suffering from ischemic heart disease, such as atherosclerosis, prior to, during or after a corrective procedure, such as cardiac bypass surgery, stenting or angioplasty. In accordance with the methods of the present invention, a fluid circuit is formed between a source of oxygenated blood, including without limitation, the left atrium, left ventricle, aorta, pulmonary vein, subclavian artery, brachiocephalic artery, radial artery or femoral artery, and the coronary venous system, so that oxygenated blood perfuses the coronary venous vasculature in a retrograde manner.

The fluid circuit of the present invention may be placed percutaneously, for example, using femoral or jugular/subclavian access sites, or intraoperatively, for example, following a sternotomy or through small openings in the chest, as in "keyhole" type CABG techniques. Blood passing through the fluid circuit may be infused with drugs, bioactive agents or angiogenic growth factors, be monitored for flow rate, pressure or other physiologic parameters, or be cooled by an external cooling system or diluted with chilled saline to induce a mild state of hypothermia (e.g., to cause a temperature drop of about 2–5° C.).

In certain embodiments, a mechanically-driven or motor-driven pump may be provided to remove a volume of blood from an oxygenated blood source and is expected to assist the left ventricle by reducing its degree of exertion. The extracted blood is then injected into the coronary venous system to improve perfusion of the myocardium. In such embodiments, control circuitry or a mechanical mechanism preferably is provided to limit a pressure-related or flow-related parameter for the flow in the coronary venous system to a value less than a predetermined value.

Figure 1:
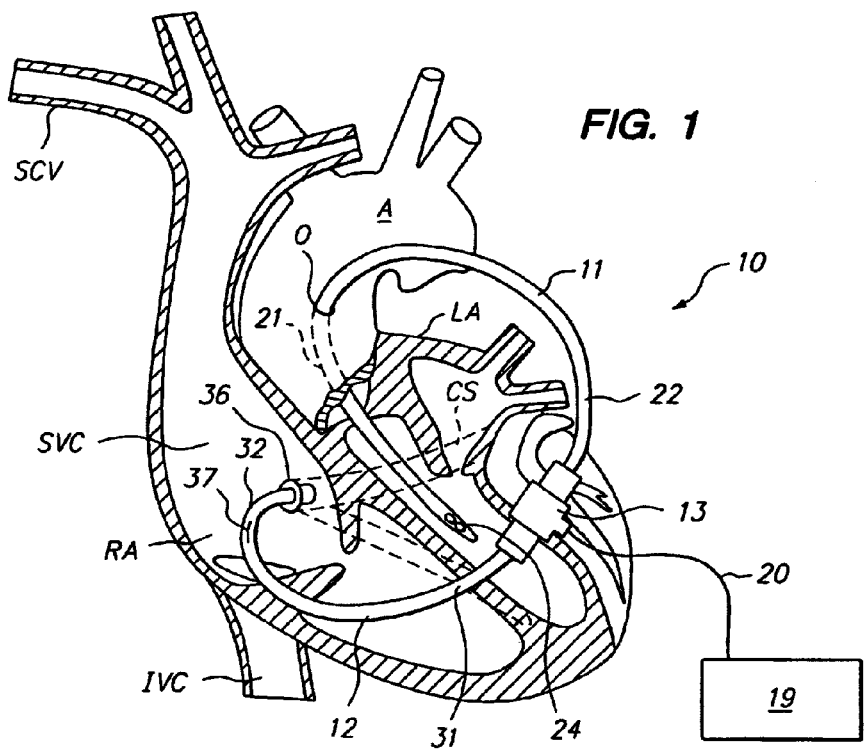
FIG. 1 is a perspective view of a human heart, partly in section, illustrating placement of a first embodiment of the apparatus of the present invention.

Referring to FIGS. 1 and 2, a first embodiment of apparatus 10 constructed in accordance with the present invention is described. Apparatus 10 comprises inlet conduit 11 and outlet conduit 12 connected by coupler 13. Coupler 13 enables the proximal end of inlet conduit 11 to be coupled to the proximal end of outlet conduit 12. Conduits 11 and 12 preferably comprise a biocompatible, flexible material typically used in catheters, for example, polyvinyl chloride, polyethylene, silicone, polyurethane or combinations thereof.

Figure 2A:
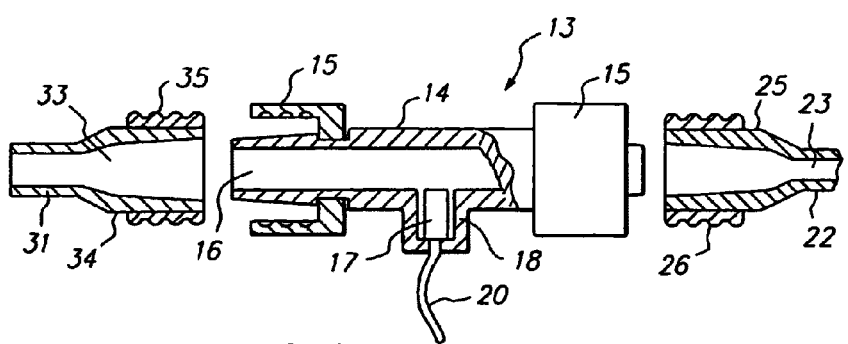
FIGS. 2A, 2B and 2C are side views, partly in section, of various embodiments of couplers for coupling together the inlet and outlet conduits of the present invention.

With respect to FIGS. 1 and 2A, coupler 13 comprises housing 14 having fittings 15 for engaging the proximal ends of conduits 11 and 12, lumen 16 and sensor 17 disposed in port 18. Sensor 17 is in turn coupled to controller 19, which may be a previously known flow, pressure or other type of monitoring system, by cable 20. Additional sensors may be incorporated into portions of inlet conduit 11, outlet conduit 12, or both, to enable computation of flow-related parameters, as described hereinafter.

Inlet conduit 11 has inlet end 21, outlet end 22 and lumen 23 connecting the inlet and outlet ends. Inlet end 21 may be intraoperatively inserted through a opening O in aorta A (or pulmonary vein, left atrium, left ventricular apex or femoral artery) and may extend through the aortic or mitral valve into left ventricle LV. Alternatively, the distal end of inlet conduit 11 simply may be left in the aorta or pulmonary vein. Opening O may be closed around inlet conduit 11 using a purse string suture (not shown), as is per se known.

Inlet end 21 preferably includes a central opening and a plurality of lateral openings in distal tip 24 that enables inlet end 21 to urged along a guide wire (not shown) to pass through the aortic or mitral valve without damaging the valve. Inlet end 21 also may include a radio-opaque marker band (not shown), for example, a gold film, that enables the location of the inlet end to be determined using a fluoroscope. Outlet end 22 is connected to coupler 13 by fitting 25, for example, threads 26 or a quick-connect coupling.

Conduit 12 has inlet end 31, outlet end 32 and lumen 33 connecting the inlet and outlet ends. Inlet end 31 is coupled to coupler 13 by fitting 34, which may also be, for example, threads 35 or a quick-connect coupling. Outlet end 32 preferably is intraoperatively inserted through an opening in superior vena cava SVC or right atrium RA, and extends through coronary ostium CO into coronary sinus CS. This opening also may be closed around the outlet conduit via a purse string suture (not shown).

Outlet end 32 preferably includes retaining means 36 for retaining the conduit in position in the coronary sinus, such as a plug, a balloon or elastomeric barbs or ribs, and also may include a radio-opaque marker band (not shown). When inserted into the coronary sinus, outlet end 32 may either partially or fully occlude the coronary ostium and permit partial flow from the coronary sinus into the right atrium. Retaining means 36, if present, preferably comprises an elastomeric material, such as silicone.

Alternatively, instead of disposing outlet end 32 of conduit 12 in the coronary sinus, outlet end 32 may be advanced through the coronary sinus into another portion of the cardiac venous vasculature, for example, great cardiac vein GCV, to provide more localized retroperfusion of the myocardium. In this case, retaining means 36 may be configured so that outlet conduit 12 passes through it a predetermined distance. Alternatively, retaining means 36 omitted entirely.

As described hereinbelow, outlet conduit 12 also may include one or more slit openings 37 for venting a portion of the blood from conduit 12 into the right atrium, for example, so as to maintain the pressure in the coronary venous system below some predetermined value, e.g., 40 mm Hg. Some of the literature suggests that 40 mm Hg is the maximum peak pressure sustainable in the coronary venous system without causing edema.

It is expected that when placed in the heart, apparatus 10 will provide short-term retrograde perfusion of the myocardium using the cardiac venous system, and will cause a redistribution of flow within the venous system so that a greater fraction of the deoxygenated blood exits via the lymphatic system and the Thebesian veins. While the venous system is not co-extensive with the coronary arteries (particularly with respect to the right ventricle), it is nevertheless expected that the method and apparatus of the present invention will provide short-term relief and preservation of ischemic myocardium in the majority of cases, since right ventricular infarcts are less common.

In addition to the foregoing uses, apparatus 10 may be advantageously used prior to corrective surgery in a diagnostic role. Specifically, regions of left ventricle dysfunction may be determined by comparing the distribution of nuclear isotopes, such as Technicium and Thallium, when the heart is at rest or stressed, to the distribution of isotopes observed after a period of retroperfusion via the coronary venous system. Such comparisons may yield important information with respect to, for example, how many bypass grafts are required and preferred locations for placement of such grafts, as described in the above-mentioned article to Udelson.

In accordance with one aspect of the present invention, apparatus 10 may be placed shortly before surgery for diagnostic purposes via a percutaneous, transluminal approach. Apparatus may then be left in position during a beating heart procedure, such as keyhole CABG or angioplasty, to perfuse and/or mildly cool (e.g., a temperature drop of about 2–5° C.) the myocardium to preserve ischemic regions. In particular, if a CABG procedure is being performed, the distal end of a graft may first be anastomosed to the cardiac artery distal to the occluded region. Inlet catheter 11 may then be withdrawn through opening O, and the proximal end of the graft anastomosed to the opening in aorta A, thus reducing the number of entry points into the aorta required to complete the bypass procedure.

Figure 2B:
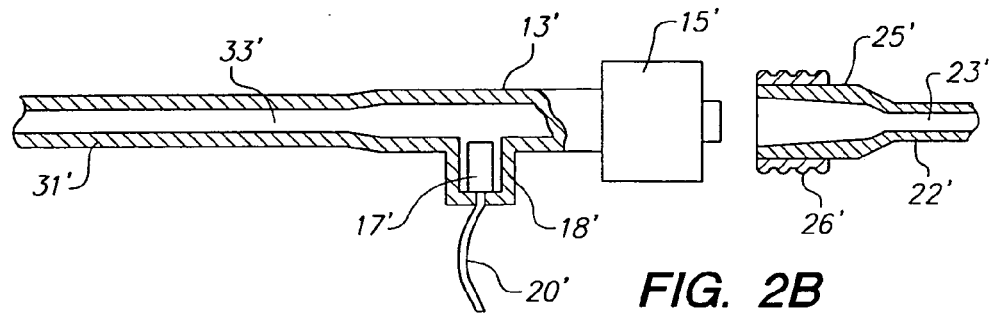

In FIG. 2B, alternative illustrative coupler 13' is incorporated into inlet end 31' of outlet conduit 12', so that outlet end 22' of inlet conduit 11' and outlet end 31' of outlet conduit 12' can be directly connected to one another. In this embodiment, coupler 13' includes fitting 15' that engages fitting 25' of outlet end 22', for example, by threads 26'. Coupler 13 also includes port 18' housing sensor 17' coupled to cable 20', for the purposes described hereinabove.

Figure 2C:
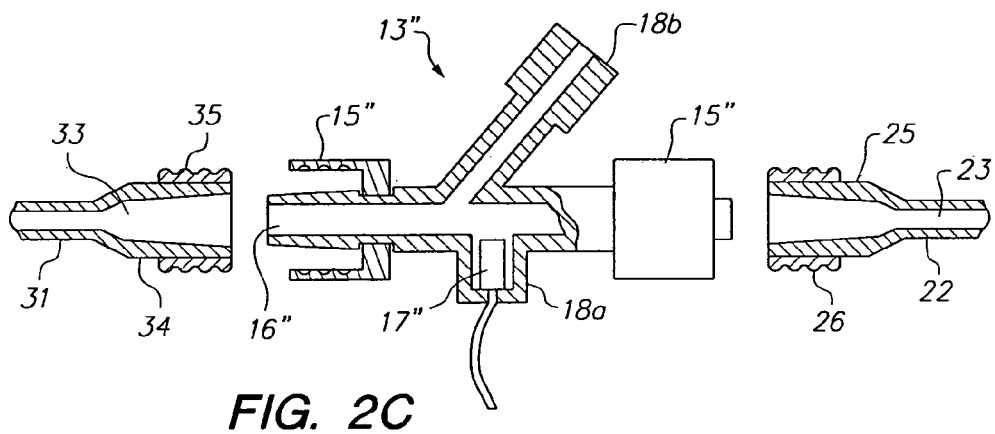

With respect to FIG. 2C, a further alternative embodiment of a coupler suitable for use with the present invention is described. Coupler 13" is similar in construction to the embodiment of FIG. 2A, but includes injection port 18b in addition to port 18a housing sensor 17". Inlet end 31 of outlet conduit 12, and outlet end 22 of inlet conduit 11 connect to coupler 13" via fittings 15", while lumen 16" provides fluid communication between outlet end 22", inlet end 31" and ports 18a and 18b. Port 18b preferably includes a valve or seal, e.g., such as a Touhy-Borst valve, that permits the lumen of port 18b to be selectively opened and closed. Accordingly, port 18b may be used to inject drugs, bioactive agents, angiogenic growth factors, genes or cooled saline into the blood passing either manually or over a predetermined time using controller 19. Alternatively, coupler 13" may be integrally formed with one or the other of outlet end 22 or inlet end 31.

As a further alternative, any of the foregoing couplers 13, 13' or 13" may enclose a pump, which may be constructed in accordance with known techniques used in previously known infusion pumps, such as the Baxter Flow-Gard 6201, Baxter International, Deerfield, Mich., or previously known centrifugal pumps, such as those manufactured by Sarns, Inc., Ann Arbor, Mich. In such an embodiment, controller 19 may control operation of the pump responsive to user selected input.

Figure 3:
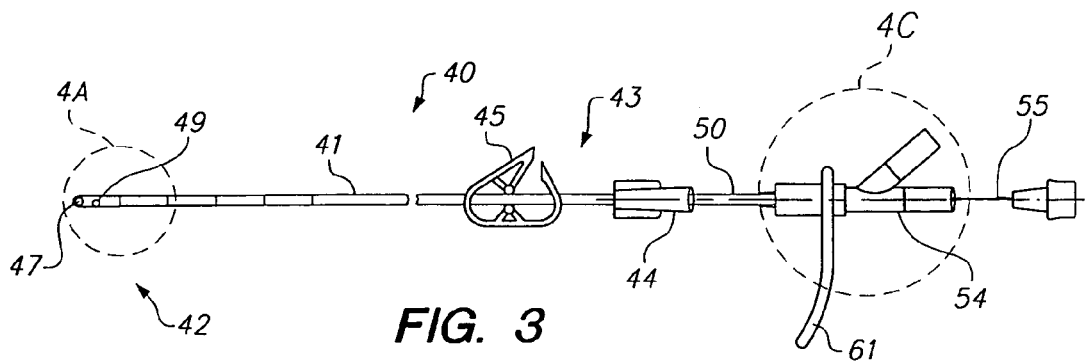
FIG. 3 is a side view of an inlet conduit constructed in accordance with the present invention.
Figure 4A:
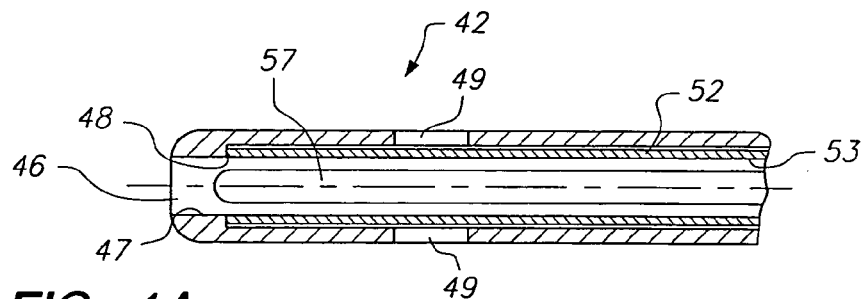
Figure 4B:
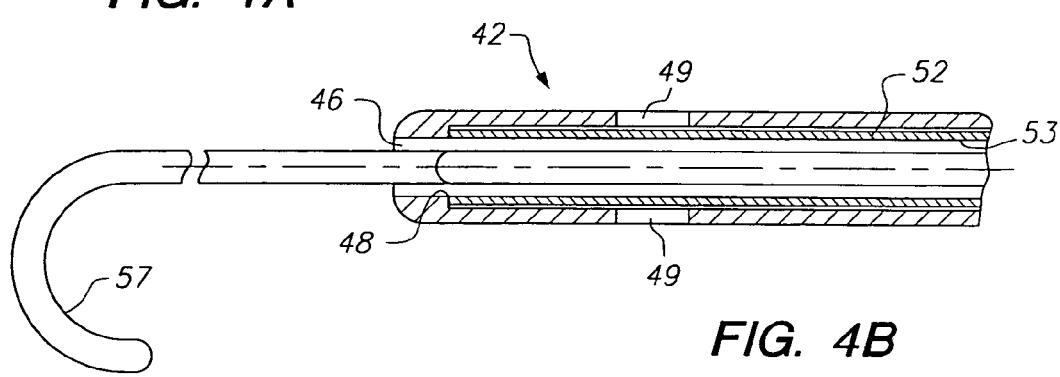
Figure 4C:
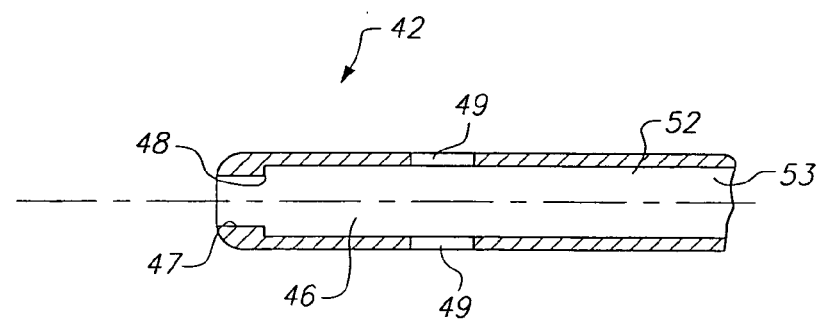
Figure 4D:
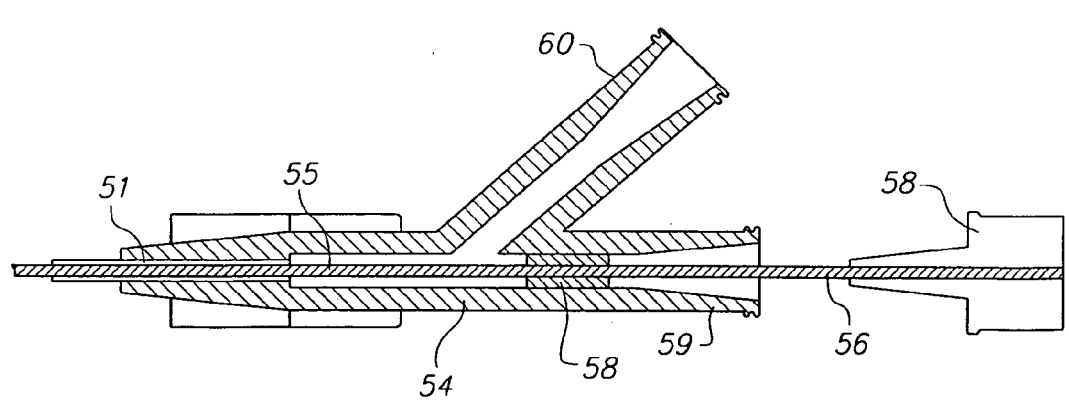
FIG. 4D is a detailed sectional view of the proximal end of the inlet conduit of FIG. 3.

Referring now to FIGS. 3 and 4, a first embodiment of an inlet conduit constructed in accordance with the principles of the present invention is described. Inlet conduit 40 comprises catheter 41 having distal end 42 and proximal end 43. Proximal end 43 includes fitting 44 configured to be coupled to coupler 13. Pinch valve 45 is disposed along catheter 41 to selectively stop flow in the catheter once it is placed. As best illustrated in FIG. 4C, catheter 41 includes lumen 46, while distal end 42 includes central opening 47 having shoulder 48, and lateral openings 49.

Stylet 50 comprises a tubular member having proximal end 51, distal end 52, and lumen 53, and is affixed to housing 54. Stylet 50 is disposed for slidingly movement within lumen 46 of catheter 41. When translated fully in the distal direction, distal end 52 of stylet 50 abuts against shoulder 48 of catheter 41, thus sealing lateral openings 49 from communication with lumen 46 (compare FIGS. 4A and 4C). In this manner, stylet 50 provides some rigidity to catheter 41 to assist in inserting and advancing the catheter into a source of arterial blood, such as the aorta, pulmonary vein, left atrium, or left ventricle. In addition, because stylet 50 seals lateral openings 49 during insertion of catheter 41 through opening O, blood entering the lumen 46 cannot escape through lateral openings 49 until stylet 50 is removed. This advantageously avoids loss of blood through lateral openings 49 during placement of inlet conduit 40.

Stylet 50 preferably comprises a malleable material, such as stainless steel or nickel-titanium, while catheter 41 preferably comprises a urethane or other plastic or elastomer capable of stretching slightly. Thus, when stylet 50 is fully inserted in lumen 46, stylet 50 bears against shoulder 48 with sufficient force that little or no blood leaks into annular gap 52 between the exterior of stylet 50 and the interior of catheter 41.

Guidewire 55 has distal end 57 and proximal end 56 coupled to knob 58. Guidewire 55 is disposed for sliding translation in lumen 46 from a retracted position, wherein distal end 57 assumes a substantially straight form within lumen 53 of stylet 50 (see FIG. 4A), and an extended position, wherein distal end 57 extends beyond the end of catheter 41 and assumes a curved non-traumatic shape (see FIG. 4B). The non-traumatic shape of distal end 57 in the extended position preferably is selected to permit guidewire 55 to pass through the aortic valve or mitral valve without injuring the valve.

Guidewire 55 may comprise, for example, a pre-stressed stainless steel wire or braid, or a nickel-titanium wire having shape-memory properties. Guidewire 55 is disposed in fluid tight seal 58 or an adjustable seal, such as a Touhy-Borst adaptor, in port 59 of housing 54 (see FIG. 4D), so that guidewire 55 may be moved between the retracted and extended positions by actuating knob 58. Guidewire 55 is selected to have sufficient clearance in lumen 53, for example 0.025 inches, that pressure may be monitored through port 60 of housing 54.

Use and operation of inlet conduit 40, stylet 50 and guidewire 55 is now illustratively described with reference to FIGS. 1, 3 and 4. After performing a sternotomy to expose aorta A, a scalpel is used to form opening O in aorta A. Distal end 42 of catheter 41 is then inserted through opening, and knob 58 is pushed in the distal direction while housing 54 is held stationary, thereby extending distal end 57 of guidewire 55. Using handle 61, stylet 50 and catheter 41 are urged forward so that distal end 42 of catheter 41 passes through the aortic valve and into left ventricle LV.

A purse string suture is formed around opening O to cinch the vessel wall against the exterior wall of catheter 41. While holding fitting 44 stationary, stylet 50 and guidewire 55 are then removed as a unit by pulling handle 61 proximally. Pinch valve 45 is then engaged to stop blood flow through lumen 46 until fitting 44 is connected to coupler 13. Once the outlet conduit is positioned, as described hereinbelow, pinch valve 45 is released, enabling blood to flow from the left ventricle to the coronary venous system.

Figure 5:
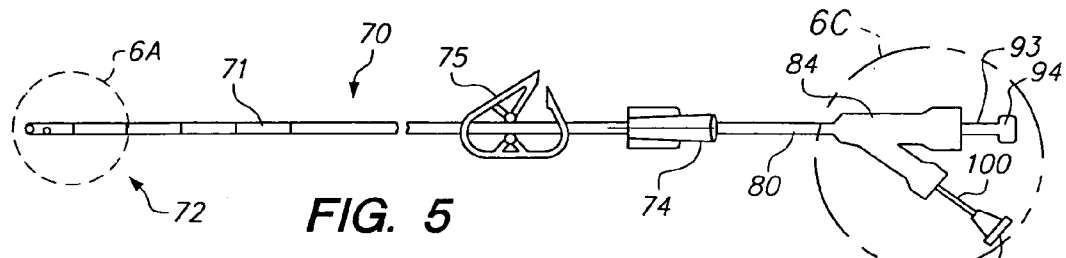
FIG. 5 is a side view of an alternative embodiment of an inlet conduit constructed in accordance with the present invention.
Figure 6A:
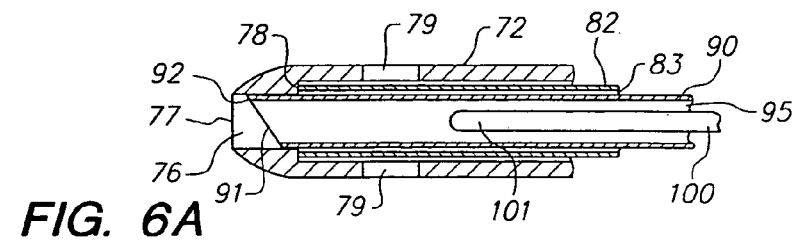
Figure 6B:
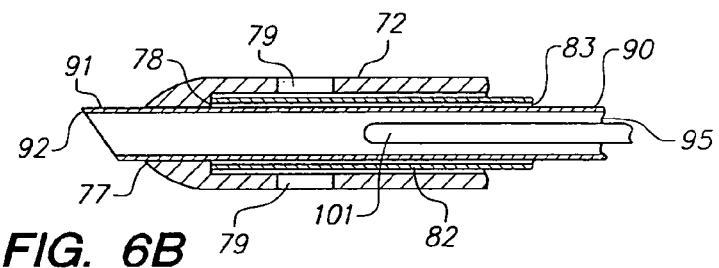

Referring now to FIGS. 5 and 6, an alternative embodiment of an inlet conduit of the present invention is described that includes a sharpened cannula for forming the opening through which the conduit is inserted into the aorta, left atrium or pulmonary vein. Inlet conduit 70 is similar in construction to inlet conduit 40 of FIG. 3, and includes catheter 71 having distal end 72 and proximal end 73. Proximal end 73 includes fitting 74 configured to be coupled to coupler 13. Pinch valve 75 is disposed along catheter 71 to selectively stop flow in the catheter once it is placed. As illustrated in FIGS. 6A and 6B, catheter 71 includes lumen 76, while distal end 72 includes central opening 77 forming shoulder 78, and lateral openings 79.

Stylet 80 comprises a tubular member having proximal end 81, distal end 82, and lumen 83, and is affixed to housing 84. Stylet 80 is disposed for slidingly movement within lumen 76 of catheter 71, and includes opening 85 aligned with lumen 86 of port 87 of housing 84. When translated fully in the distal direction, distal end 82 of stylet 80 abuts against shoulder 78 of catheter 71, thus sealing lateral openings 79 from communication with lumen 76. As in the embodiment of FIG. 3, stylet 80 provides both rigidity to catheter 71 and seals lateral openings 79 during placement of catheter 71.

As for the embodiment of FIG. 3, stylet 80 preferably comprises a malleable material, while catheter 71 preferably comprises a material capable of stretching slightly. Accordingly, when stylet 80 is fully inserted in lumen 76, stylet 80 bears against shoulder 78 to reduce the leakage of blood into the annular gap between the exterior of the stylet and the interior of catheter 71.

To obviate the need for a separate trocar to form the opening through which conduit 70 is inserted, sharpened cannula 90 is provided. Cannula 90 comprises a tubular member having distal end 91 including non-coring tip 92, proximal end 93 including fitting 94, and lumen 95. Cannula 90 has elongated skive 96 formed in the portion of proximal end 93 adjacent to lumen 86 of port 87. Cannula 90 is disposed for sliding movement within lumen 83 of stylet 80 between a retracted position, wherein non-coring tip 92 is retracted within lumen 83 of stylet 80 (see FIG. 6A), and an extended position, wherein non-coring tip 92 extends beyond the end of catheter 71 (see FIG. 6B). Skive 96 is sufficiently long that lumen 86 remains unobstructed whether cannula 90 is in the extended position or retracted position. Elastomeric sleeve 97, for example, silicone tubing, provides a fluid tight seal where cannula 90 exits housing 84.

Guidewire 100 has distal end 101 and proximal end 102 coupled to knob 103. Guidewire 100 is disposed for sliding translation in lumen 95 of cannula 90, and enters lumen 95 through seal 104, lumen 86 and skive 96. Guidewire 100 is movable between a retracted position, wherein distal end 101 assumes a substantially straight form within lumen 86 (see FIG. 6A), and an extended position (similar to FIG. 4B), wherein distal end 101 extends beyond the end of catheter 71 and assumes a curved non-traumatic shape. As for the embodiment of FIGS. 3 and 4, the non-traumatic shape of distal end 101 in the extended position preferably is selected to permit guidewire 100 to pass through the aortic valve or mitral valve without injuring the valve. Guidewire 100 may be constructed of the materials described hereinabove, and may be moved between the retracted and extended positions by actuating knob 103.

Use and operation of inlet conduit 70, stylet 80, cannula 90 and guidewire 100 is now illustratively described with reference to FIGS. 1, 5 and 6. After performing a sternotomy to expose aorta A, cannula 90 is advanced by urging fitting 94 in the distal direction while holding housing 84 stationary, thereby moving non-coring tip 92 to the extended position. Catheter 70 is then urged against the exterior wall of the aorta or pulmonary vein to form an opening therein.

Once non-coring tip 92 has penetrated the thickness of the vessel wall, and distal end 72 of catheter 71 has been inserted through the opening, fitting 94 is pulled proximally to retract cannula 90 within stylet 80. While holding housing 84 stationary, knob 103 is pushed in the distal direction, causing distal end 101 of guidewire 100 to move to the extended position. Stylet 80 and catheter 71 then are urged forward so that distal end 72 of catheter 71 passes through the aortic valve and into left ventricle LV.

After a purse string suture is formed to cinch the vessel wall against the exterior wall of catheter 71, housing 84 is pulled proximally while fitting 74 is held stationary, thus removing stylet 80, cannula 90 and guidewire 100 as a unit. Pinch valve 75 is then engaged to stop blood flow through lumen 76 until fitting 74 is connected to coupler 13. Once the outlet conduit is positioned, as described hereinbelow, pinch valve 75 is released, enabling blood to flow from the left ventricle to the coronary venous system.

Figure 6C:
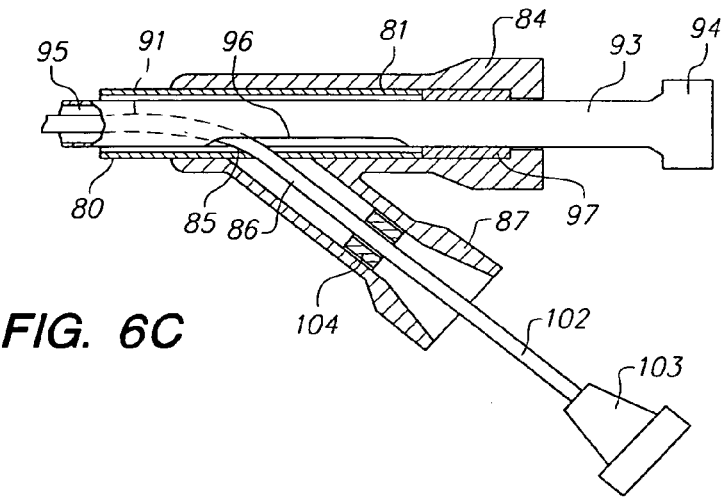
FIG. 6C is a detailed sectional view of the proximal end of the inlet conduit of FIG. 5.
Figure 7A:
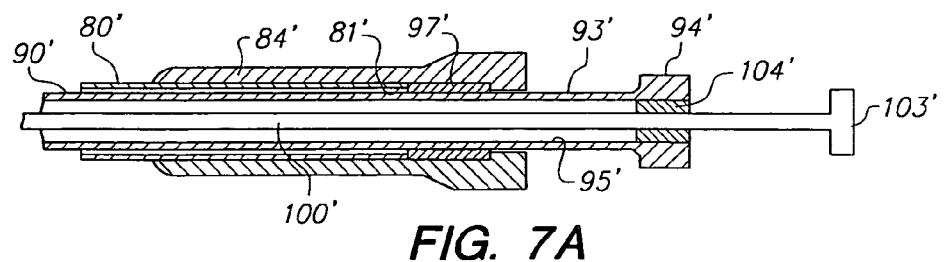
FIGS. 7A and 7B are sectional views of the proximal end of further alternative embodiments of the inlet conduit of FIG. 5.
Figure 7B:
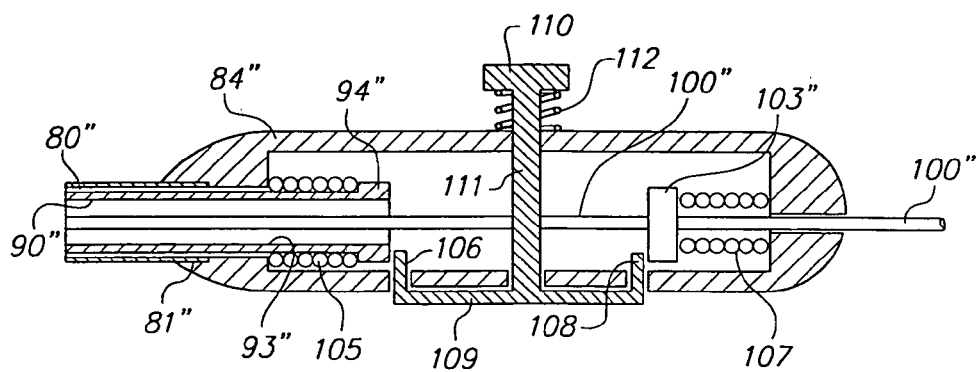

With respect to FIGS. 7A and 7B, alternative embodiments of the arrangement of the proximal ends of the stylet, cannula and guidewire of FIGS. 5 and 6 are described. In FIG. 7A, stylet 80I, cannula 90I and guidewire 100' are mounted coaxially. In this embodiment, catheter 71 remains unchanged from the embodiment of FIGS. 5 and 6, as do the proximal ends of the stylet, cannula and guidewire. By contrast, however, proximal end 81' of stylet 80' is mounted in housing 84'; proximal end 93' of cannula 90' is slidingly disposed in lumen 83' of stylet 80' and is sealed by elastomeric tube 97'; and guidewire 100' is slidingly disposed in lumen 95' of cannula 90' in seal 104'. Cannula 90' is actuated by fitting 94' and guidewire 100' is actuated by knob 103'. Operation of the embodiment of FIG. 7A will be apparent by comparison to the description set forth hereinabove with respect to the embodiment of FIG. 6C.

With respect to FIG. 7B, another alternative embodiment is described, wherein the stylet, cannula and guidewire are arranged coaxially for single-button operation. In FIG. 7B, catheter 71 remains unchanged from the embodiment of FIGS. 5 and 6, as do the proximal ends of the stylet, cannula and guidewire. In this embodiment, however, proximal end 81" of stylet 80" is affixed to housing 84"; proximal end 93" of cannula 90" includes hub 94"; and guidewire 100" includes hub 103". Hub 94" is held compressed against the bias of spring 105 by stop 106, while hub 103" is held compressed against the bias of spring 107 by stop 108. Stops 106 and 108 are connected to member 109, which in turn is connected to push button 110 by member 111. Push button 110 is biased upwards by spring 112.

Operation of the embodiment of FIG. 7B is as follows: Catheter 71 is pre-loaded on stylet 80", which has its non-coring tip locked in the extended position by stop 106. Once the opening is formed in the aorta, pulmonary vein, left atrium or left ventricle, push button 110 is depressed. This in turn causes stops 106 and 108 to move out of engagement with hubs 94" and 103", respectively. When hub 94" is released by stop 106, spring 105 causes cannula 90" to become retracted within stylet 80".

Simultaneously, when stop 108 releases hub 103", spring 107 urges guidewire 100" to the extended position, thus enabling further insertion of the inlet conduit through the aortic valve or mitral valve, if desired. Once the catheter is deployed in the heart, stylet 80", cannula 90" and guidewire 100" may be removed as a unit by pulling housing 84" proximally while holding fitting 74" of catheter 71: stationary. The remainder of the placement procedure is as described elsewhere above.

As will be apparent to one of ordinary skill, the push button actuation mechanism of FIG. 7B is intended to be illustrative, and other mechanisms, such as those involving levers, linkages, or rotational movements of the components may be readily substituted for the mechanism of FIG. 7B. For example, stops 106 and 107 could be replaced by linked levers, or hubs 94" and 103" may include projections that ride in corresponding longitudinal and circumferential grooves in the interior surface of housing 84". While the mechanism of FIG. 7B is illustrated with respect to a coaxial arrangement of the cannula and guidewire, one of ordinary skill will recognize that the above-described mechanisms may be readily implemented for the Y-port arrangement depicted in FIG. 6C.

Figure 8:
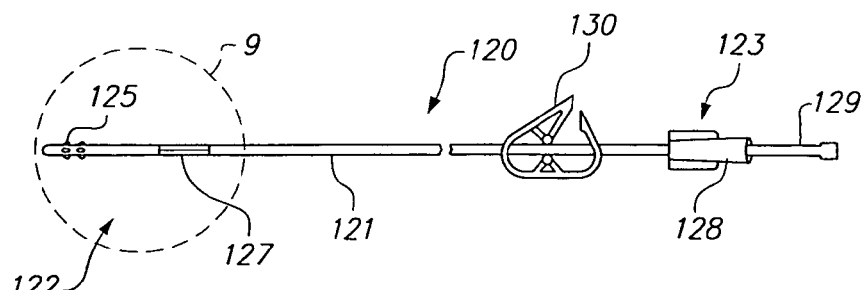
FIG. 8 is a side view of a outlet conduit constructed in accordance with the present invention.
Figure 9:
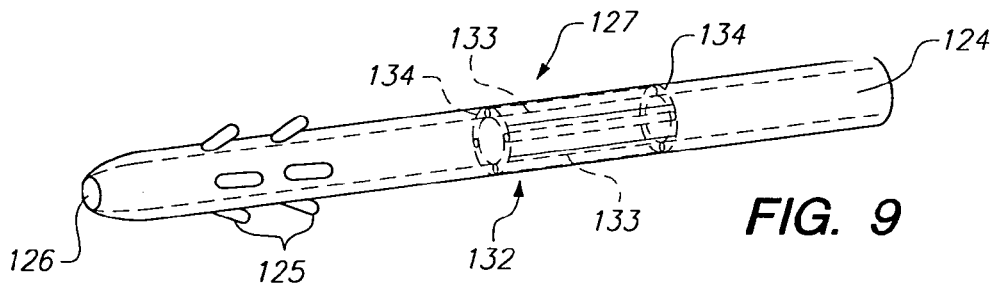
FIG. 9 is a detailed perspective view of the distal end of the outlet conduit of FIG. 8.

Referring now to FIGS. 8 through 10, a preferred embodiment of outlet conduit 120 is described. Outlet conduit 120 comprises catheter 121 having distal end 122, proximal end 123 and lumen 124. Distal end 122 includes retaining means 125, illustratively elastomeric barbs or spikes, for retaining distal end 122 within the coronary sinus. Retaining means 125 may of course include other shapes, such as ribs, balloons or tubular plugs. Distal end 122 also includes opening 126 communicating with lumen 124, and slit valve 127, described hereinbelow.

Proximal end 123 has fitting 128 for connecting to coupler 13 (see FIG. 1), and guidewire 129 may be disposed in lumen 124 to assist in inserting distal end 122 through the coronary ostium. Pinch valve 130 reduces blood loss while fitting 128 is coupled to coupler 13. Slit valve 127 is located on catheter 121 adjacent to distal end 122, so that the slit valve is disposed unobstructed in the right atrium when outlet conduit is placed.

Figure 10A:
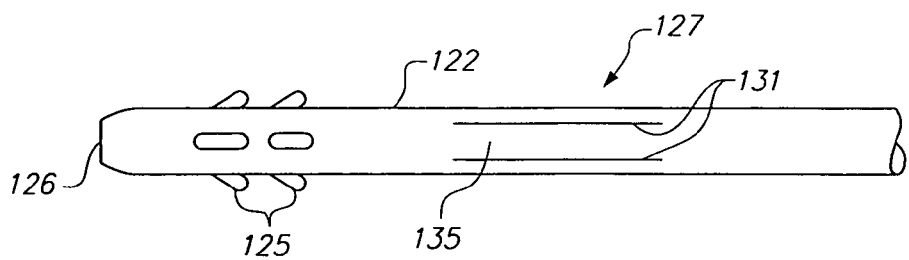
FIGS. 10A and 10B are detailed side views of the distal end of the outlet conduit of FIG. 8 illustrating operation of the slit valve of the present invention.
Figure 10B:
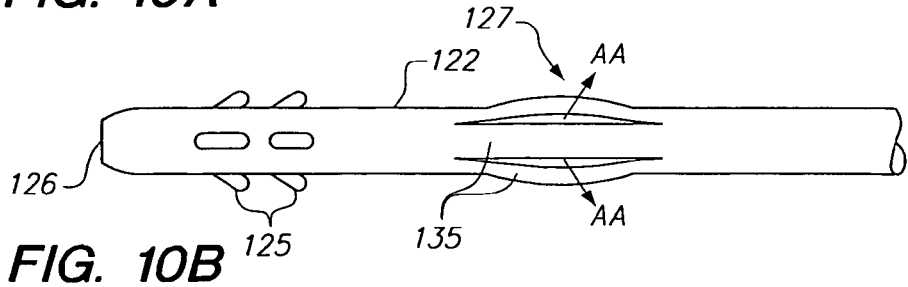

With respect to FIGS. 10A and 10B, slit valve 127 comprises a series of circumferentially spaced-apart through-wall slits 131, for example, four slits spaced apart 90°. Because slits 131 structurally weaken the catheter wall, flexing of the catheter may cause the valve to open inadvertently. Accordingly, to strengthen the wall of catheter 121 in the region of slits 131, reinforcing cage 132 is affixed to catheter 121 in registration with slits 131. Cage 132 comprises, for example, struts 133 welded at either end to washers 134. The entire assembly may then be embedded in the wall of catheter 121, as illustrated in FIG. 9, or affixed to the interior or exterior surface of the catheter wall. Preferably, cage 132 is positioned relative to slits 131 so that struts 134 are circumferentially offset from slits 131.

The material of walls 135, and the size, number and spacing of slits 131 may be selected so that walls 135 between slits 131 bulge outward only when the pressure within the catheter exceeds a predetermined pressure, thereby permitting some of the blood to be vented (illustrated by arrows AA in FIG. 10B). For example, as stated hereinabove, some literature suggests that the coronary venous system is susceptible to edema at pressures above 40 mm Hg. Accordingly, slit valve 127 may be configured so that walls 135 bulge outward to permit blood to be vented into the right atrium until the pressure within the catheter falls below 40 mm Hg.

Use and operation of catheter 121 is now described with respect to FIGS. 1 and 8. After placement of the inlet conduit, the right atrium or superior vena cava is exposed, and an opening is made with a conventional trocar or scalpel. Catheter 121 is then inserted along guidewire 129 until distal end 122 is inserted through the coronary ostium. Catheter 121 is then positioned so that retaining means 125 engages the interior wall of the coronary sinus, or other portion of the venous vasculature, and slit valve 127 is located within the right atrium. Guidewire 129 is then removed, fitting 128 is connected to coupler 13, and pinch valve 130, if present, is released.

Figure 11:
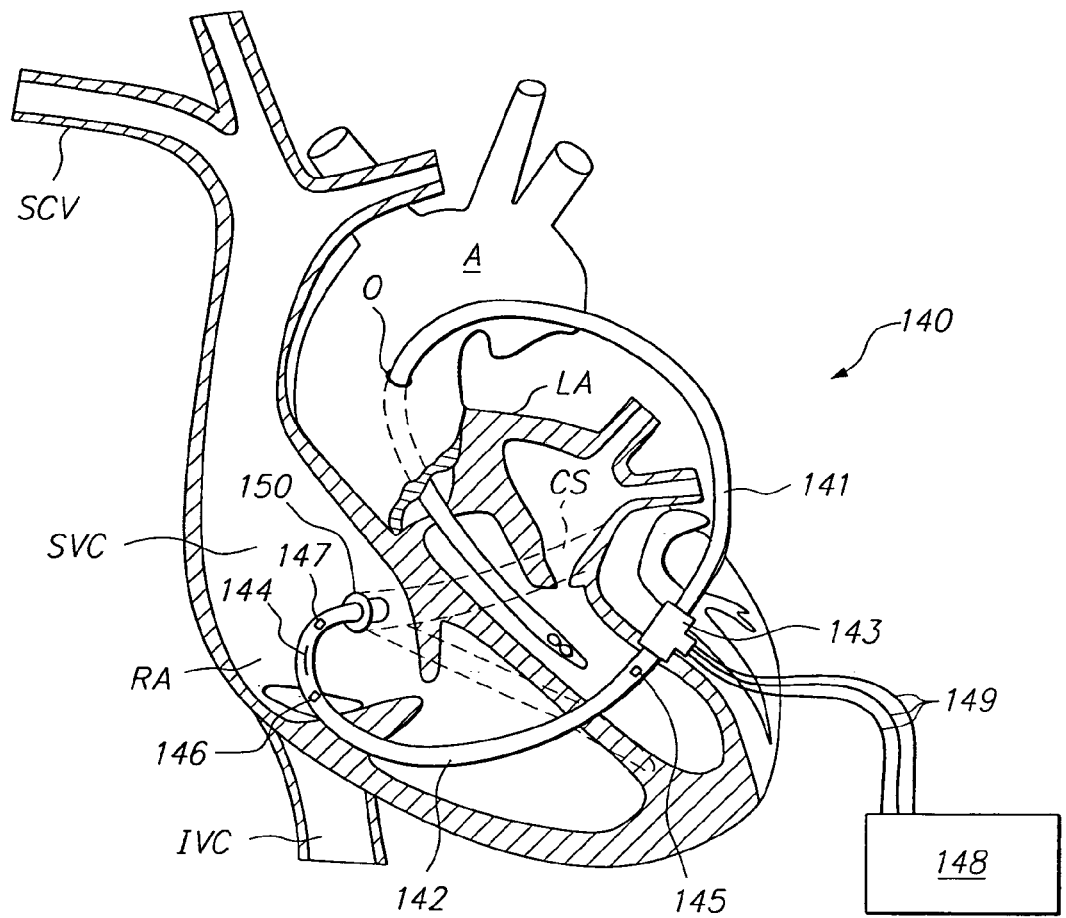
FIG. 11 is a perspective view of a human heart, partly in section, illustrating placement of another alternative embodiment of the apparatus of the present invention.

Referring now to FIG. 11, another preferred embodiment of the apparatus and methods of the present invention is described. Apparatus 140 comprises inlet conduit 141 and outlet conduit 142 having integral coupler 143. Coupler 143 enables the proximal end of inlet conduit 141 to be coupled to the proximal end of outlet conduit 142. Conduits 141 and 142 preferably are constructed as described hereinabove with respect to FIG. 1, and outlet conduit 142 preferably includes slit valve 144 described hereinabove with respect to FIGS. 8–10.

In accordance with this aspect of the present invention, outlet conduit 142 includes sensors 145, 146 and 147 for measuring flow-related parameters, such as pressure or flow rate. Sensors 145 to 147 may comprise piezoelectric crystals, transducers, or other suitable sensor technology, as described, for example, in U.S. Pat. No. 5,085,223 to Lars et al. or U.S. Pat. No. 5,195,375 to Tenerz et al. Sensors 145 to 147 are electrically coupled to controller 148 via wires 149. Controller 148 includes either analog or digital circuitry, or both, for monitoring and/or computing a flow-related parameter for fluid passing through outlet conduit 142.

Illustratively, for the embodiment of FIG. 11, sensors 145 and 146 may be configured to measure the pressure in outlet conduit. Accordingly, using fluid mechanics equations that are per se known, the pressure values at sensor locations 145 and 146 may be used to compute the flow rate of blood passing through outlet conduit 142. In addition, the reduction in pressure measured between sensors 146 and 147 may be used to determine the rates of blood flow into the coronary sinus through distal end 150 of outlet catheter 142, and through slit valve 144.

Alternatively, if slit valve 144 is omitted, sensor 146 may be omitted, in which case the flow rate through outlet conduit 142 may be computed based on the pressure drop observed between sensors 145 and 147. Other arrangements of two or more sensors on inlet conduit, outlet conduit, or the coupler, or combinations thereof, will be apparent, and may be used to measure or compute various flow-related parameters for the flow through the circuit formed by inlet conduit 141 and outlet conduit 142.

Figure 12:
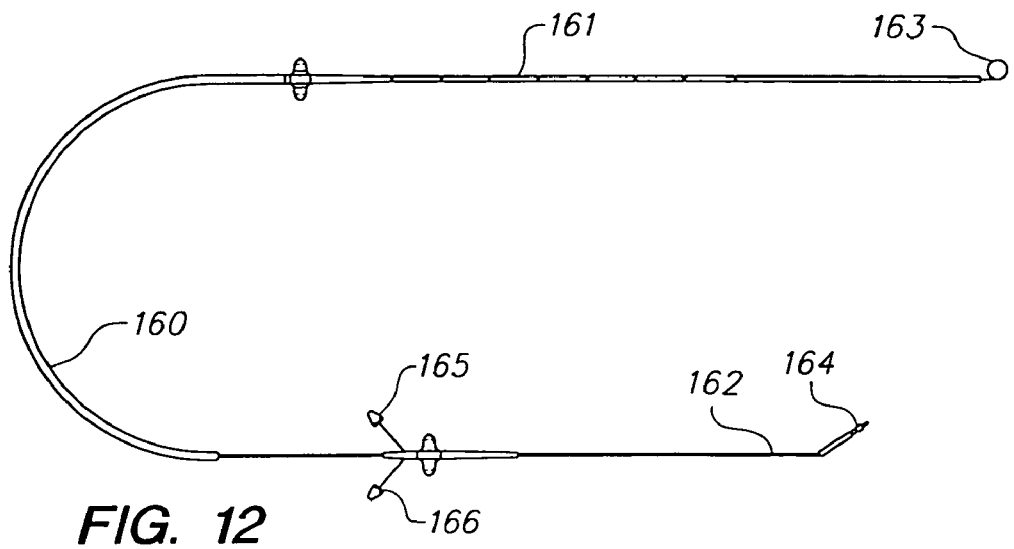
FIG. 12 is a plan view of a further alternative embodiment of apparatus constructed in accordance with the present invention.

Referring now to FIG. 12, a further alternative embodiment of the apparatus of the present invention is described. Apparatus 160, which preferably comprises unitary catheter 160, includes inlet conduit portion 161, outlet conduit portion 162 and guidewire 163. Compared to the embodiment of FIG. 2A, apparatus 160 includes a coupler that comprises an intermediate length of conduit disposed between inlet conduit portion 161 and outlet conduit portion 162. Apparatus 160 preferably includes a retaining element 164, such as the elastomeric ribs, barbs, etc., described hereinabove disposed on outlet conduit portion 162 to retain that end of the device in the coronary venous vasculature. Apparatus 160 also may include infusion or pressure monitoring port 165 and inflation port 166, for example, where retaining element is inflatable. Inlet conduit portion 161 is configured to be inserted into an oxygenated blood source.

Apparatus 160 is configured for percutaneous insertion along guidewire 163 by first placing outlet conduit portion through the coronary sinus and into the venous vasculature, e.g., via the femoral vein, inferior vena cava, and right atrium. Guidewire 163 is then withdrawn, and inlet conduit portion may then be inserted via a cutdown into the femoral artery. The unitary construction of apparatus 160 is expected to pose less risk of thrombogenicity than the separately coupled conduits, for example, of FIG. 11. Outlet conduit portion 162 also may include a valve like that of FIGS. 9 and 10 to limit flow or pressure into the venous vasculature.

Figure 13A:
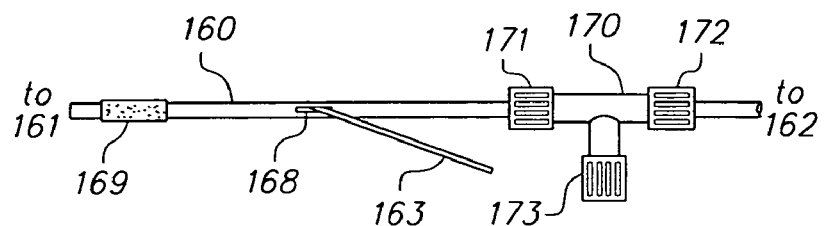
FIGS. 13A–13C are side views of a portion of the apparatus of FIG. 12 illustrating use of a side port.
Figure 13B:
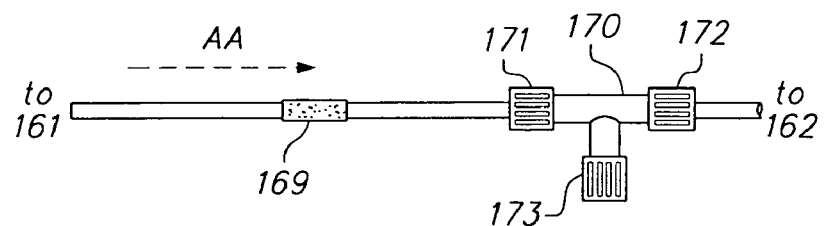
Figure 13C:
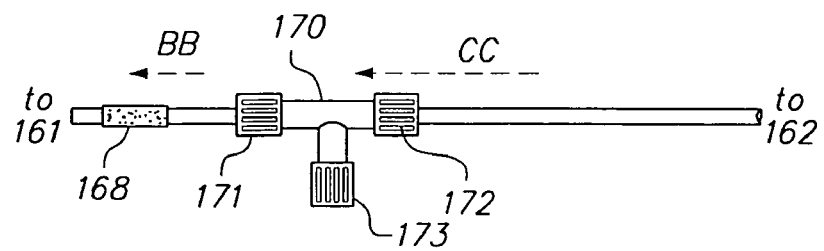

With respect to FIGS. 13A to 13B, an alternative embodiment of apparatus 160 is described that enables inlet conduit portion 161 of the apparatus to be percutaneously placed. FIG. 13A, shows portion 167 of apparatus 160 located between inlet conduit portion 161 and outlet conduit portion 162. Portion 167 includes through-wall hole 168, elastomeric hemostatic sleeve 169, and hemostatic port 170. Hemostatic port 170 includes hemostatic clamps 171 and 172 and coupling 173. As illustrated in FIG. 13A, guidewire 163 exits the central lumen of apparatus 160, thereby enabling inlet conduit portion 161 of apparatus to be percutaneously inserted and advanced within, for example, the aorta, left atrium or left ventricle.

Once inlet conduit portion 161 is placed, guidewire 163 is withdrawn through hole 168, and the clinician slides hemostatic sleeve 169 in direction AA in FIG. 13B to seal hole 168. Later, if it is desired to infuse drugs or bioactive agents into blood passing through apparatus 160, the clinician slides hemostatic sleeve 169 in direction BB and then slides hemostatic port 170 over hole 168 in direction CC. Hemostatic clamps 171 and 172 on hemostatic port 170, which may operate on the principle of compression-type fittings, are then actuated, and an infusion pump or other device of interest (not shown) is coupled to hemostatic port 170 using coupling 173.

Referring now to FIGS. 14 to 17, another embodiment of apparatus constructed in accordance with the present invention is described. Apparatus 180 comprises conduits 190 and 200 coupled to motor-driven pump 182. Control circuitry 184 controls operation of pump 182 responsive to user selected input. Pump 182 includes inlet port 185 and outlet port 186, and may be constructed in accordance with known techniques used in previously known infusion pumps, such as the Baxter Flow-Gard 6201, Baxter International, Deerfield, Mich., or previously known centrifugal pumps, such as those manufactured by Sarns, Inc., Ann Arbor, Mich.

Figure 16:
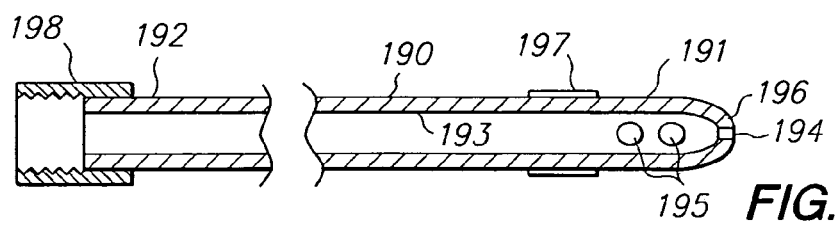
FIG. 16 is a sectional view of a first conduit of the apparatus of FIG. 14.

Conduit 190 has inlet end 191, outlet end 192 and lumen 193 connecting the inlet and outlet ends (see FIG. 16). Inlet end 191 may be transluminally inserted via the right internal jugular vein J (or alternatively, right subclavian vein SCV) and superior vena cava SVC into the right atrium RA, and extends through a puncture in the atrial septum S into the left atrium LA. Inlet end 191 preferably includes central opening 194, plurality of lateral openings 195, and bullet-shaped or conical-shaped tip 196 that enables inlet end 191 to urged along a guide wire (not shown) to penetrate the atrial septum. Inlet end 191 also preferably includes a radioopaque marker band 197, for example a gold film, that enables the location of the inlet end to be determined using a fluoroscope. Outlet end 192 is coupled to inlet 185 of pump 182 by fitting 198, for example, threads or a quick-connect coupling.

Alternatively, inlet end 191 of conduit 190 may be inserted transluminally and transseptally, as described hereinabove, and then passed through the mitral valve from the left atrium into the left ventricle. It is expected that short-term use of conduit 190 in this manner will not adversely effect the mitral valve. As yet another alternative, described hereinafter with respect to FIG. 19, inlet end 191 of conduit 190 may be inserted transluminally via the femoral artery and aorta into the aortic root, or through the aortic valve into the left ventricle.

Figure 17:
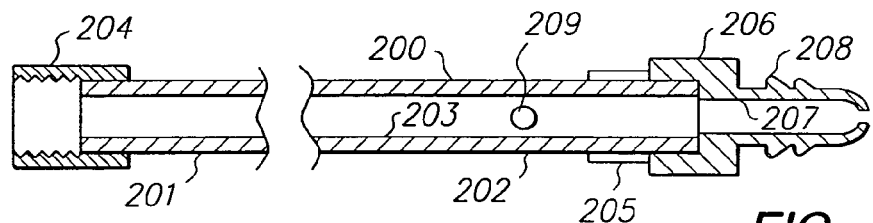
FIG. 17 is a sectional view of a second conduit of the apparatus of FIG. 14.

Conduit 200 has inlet end 201, outlet end 202 and lumen 203 connecting the inlet and outlet ends (see FIG. 17). Inlet end 201 is coupled to outlet port 186 of pump 182 by fitting 204, which may also be, for example, threads or a quick-connect coupling. Outlet end 202 is transluminally inserted via the right subclavian vein SCV (or right internal jugular vein J) and superior vena cava SVC into the right atrium RA, and extends through the coronary ostium CO into the venous vasculature. Outlet end 202 preferably includes radio-opaque marker band 205 and plug 206. Plug 206 has bore 207 and one or more retaining elements 208, for example, a plurality of barb or rib-type projections, that engage the interior wall of the venous vasculature to retain the plug in the coronary sinus until forcibly removed. When inserted into the venous vasculature, outlet end 202 may either partially or fully occlude the coronary ostium and permit partial flow through the coronary ostium into the right atrium.

Outlet end 202 may be advanced through the coronary ostium and into the cardiac venous vasculature, for example, the great cardiac vein GCV, to provide localized retroperfusion of the myocardium. In this case, plug 206 may be configured so that conduit 200 passes through it a predetermined distance, or plug 206 may be omitted entirely. In addition, conduit 200 may include one or more openings 209 for venting a portion of the blood from conduit 200 into the right atrium, for example, when the volume of blood drained from the left atrium or left ventricle to reduce left ventricle exertion is greater than the volume needed to perfuse the venous system.

Conduits 190 and 200 preferably comprise a biocompatible, flexible material typically used in catheters, for example, polyvinyl chloride, polyethylene or silicone. Conduit 200 is preferably more rigid than conduit 190, so that plug 206, if present, may be removably seated in coronary ostium CO by exerting force on inlet end 201 of the conduit. Plug 206 preferably comprises an elastomeric material, such as rubber, latex or silicone.

Control circuitry 184 may be constructed in accordance with previously known designs for circuitry used in controlling infusion pumps, and permits a clinician to input a duty cycle that specifies intervals of activation and deactivation of the pump. Control circuitry 184 cyclically activates and deactivates pump 182 responsive to the input duty cycle. Control circuitry 184 also preferably includes circuitry for measuring the flow rate and pressure of blood flowing through conduit 200, and accordingly may accept as input limit values pressure-related or flow-related parameters, for example, peak pressure, mean pressure, or maximum flow rate. Activation of pump 182 is then controlled so that a measured or computed parameter (based on the measured pressure or flow in conduit 200) does not exceed the limit values.

Thus, for example, control circuitry 184 may accept as an input limit values a value of 40 mm Hg for the peak pressure and a value of 5–100 ml/min for the maximum flow rate attained in conduit 200. Some of the literature suggests that 40 mm Hg is the maximum peak pressure sustainable in the coronary venous system without causing edema of the veins. Control circuitry 184 monitors, via a suitable flow probe disposed on or in conduit 200, the pressure and flow rate in the conduit and shuts off or reduces the speed of pump 182 to maintain the peak pressure and flow rate in the coronary venous system below the input limit values.

Figure 14:
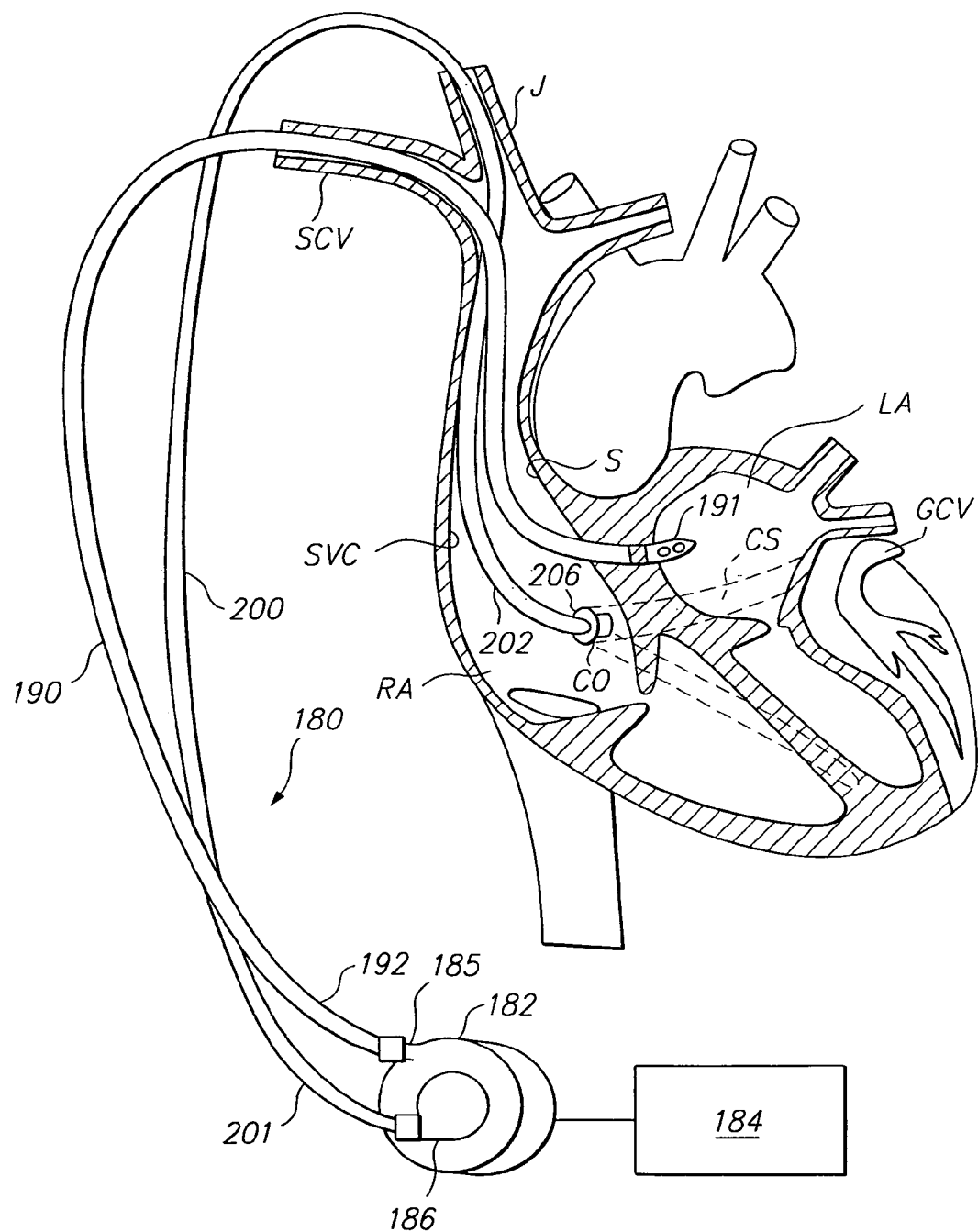
FIG. 14 is a perspective view of a human heart, partly in section, illustrating implantation of an embodiment of the apparatus of the present invention including an extracorporeal pump.
Figure 15:
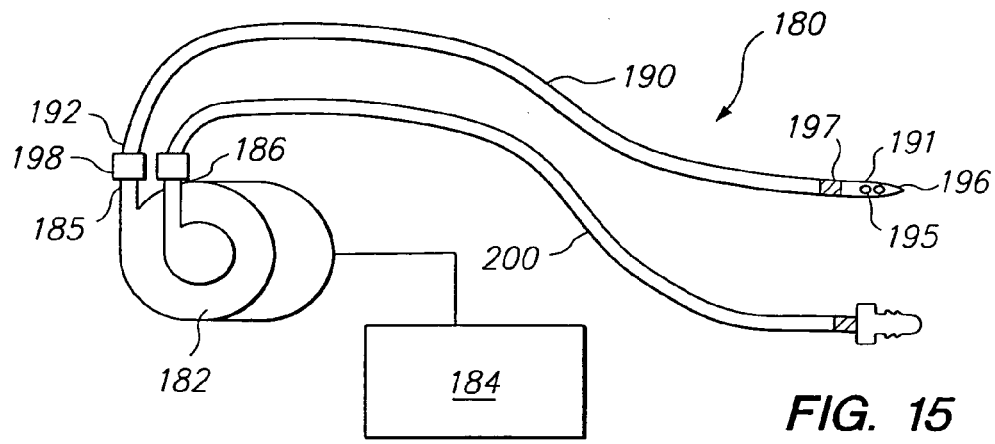
FIG. 15 is a perspective view of the apparatus of FIG. 14.

Referring still to FIG. 14, implantation of apparatus 180 in accordance with the methods of the present invention is now described. Conduit 190 may be implanted using a transluminal approach that is a variation of the Brockenbrough method of catheterizing the left ventricle. The conventional Brockenbrough technique, which is described in CARDIAC CATHETERIZATION AND ANGIOGRAPHY, W. Grossman, ed., at pages 63–69, published by Lea & Febiger, Philadelphia (1980), employs a catheter and needle combination that is advanced through the right femoral artery and into the right atrium, and used to puncture the septum between the right and left atria.

In accordance with the present invention, a Brockenbrough needle kit, available from United States Catheter and Instrument Corp., Billerica, Mass., is advanced over a guide wire into the right atrium via the right internal jugular vein using a standard Seldinger technique. The Brockenbrough needle is used to puncture the atrial septum, and the transseptal puncture is then dilated using, for example, progressively larger diameter catheters, which are then withdrawn, leaving the guide wire in place.

Next, conduit 190 is slipped over the proximal end of the guide wire, via central opening 194, so that the guide wire passes through lumen 193 and exits through fitting 198. Conduit 190 is then advanced over the guide wire so that inlet end 191 passes through the transseptal puncture and into the left atrium, as determined, for example, by visual confirmation of the location of marker band 197 using a fluoroscope. If desired, the clinician may advance inlet end 191 of conduit 190 through the mitral valve and into the left ventricle. Once inlet end 191 of conduit 190 is positioned in the left atrium or left ventricle, the guide wire is withdrawn proximally through fitting 198. Fitting 198 is then coupled to inlet port 185 of pump 182.

Using standard catheterization techniques, a guide wire is inserted transluminally via right internal jugular vein J (or alternatively, right subclavian vein SCV), through superior vena cava SVC, and into coronary sinus CS via coronary ostium CO. Conduit 200 is slipped over the proximal end of the guide wire, via bore 207 in plug 206, so that the guide wire passes through lumen 203 and exits through fitting 204. Conduit 200 is advanced over the guide wire so that plug 206 passes through coronary ostium CO and becomes lodged in coronary sinus CS. Alternatively, the clinician may advance outlet end 202 of conduit 200 through the coronary sinus and into a selected cardiac vein (e.g., great cardiac vein GCV) under fluoroscopic guidance. Once outlet end 202 of conduit 200 is positioned in the coronary venous vasculature, the guide wire is withdrawn proximally through fitting 204. Fitting 204 is then coupled to outlet port 186 of pump 182, completing implantation of the apparatus.

The clinician then inputs a desired duty cycle and any desired limit values into control circuitry 184 via a suitable input pad or keyboard. Responsive to the duty cycle and limit values input by the clinician, control circuitry 184 cyclically activates pump 182 to drain a desired volume or flow rate of blood from the left atrium or left ventricle through conduit 190, thereby partially unloading the left ventricle. Pump 182 then injects that drained volume of blood into the coronary sinus or selected cardiac vein, thereby providing retrograde perfusion of the myocardium that reduces infarction of the ischemic region of myocardium. It is expected that apparatus 180 will infuse the venous system with blood at flow rates of 5–100 ml/min. Higher rates of drainage from the left atrium or left ventricle may be attained where conduit 200 includes openings 209 (see FIG. 17) for venting a portion of the blood into the right atrium.

Figure 18:
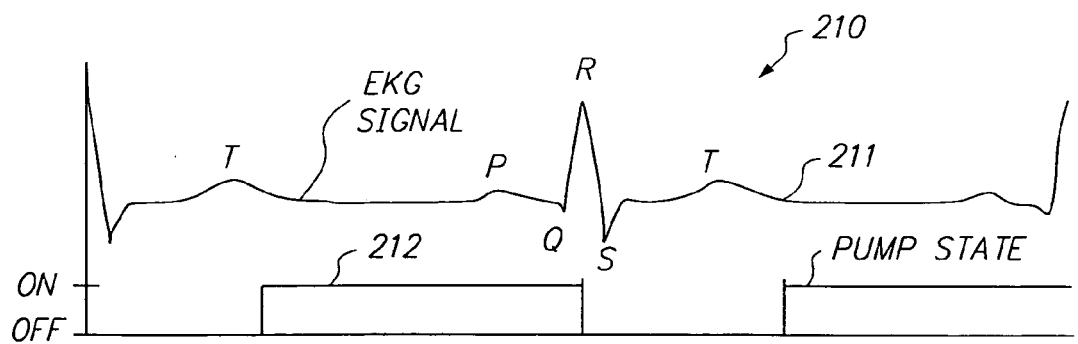
FIG. 18 is a timing diagram showing an illustrative duty cycle for activation of the pump of the apparatus of FIG. 14.

Referring now to FIG. 18, an exemplary duty cycle 210 that may be input to control circuitry 184 is described. Waveform 211 of FIG. 18 is that obtained from an electrocardiograph, while waveform 212 corresponds to the on/off state of pump 182. It is contemplated that one mode of operation of pump 182 will be to synchronize operation of the pump, and hence injection of blood into the coronary venous system, with the period of diastole. Thus, for example, control circuitry 184 will switch pump 182 on at the completion of systole (corresponding to the T-wave) and off at the offset of the QRS complex, in a manner similar to that employed in synchronized retroperfusion. Alternatively, control circuitry 184 may activate pump 182 only during systole.

As a yet further alternative, the duty cycle input into control circuitry 184 may require pump 182 to be continuously active for several seconds, alternating with several seconds of rest (e.g., 15 seconds on, followed by 4 seconds off). In this case, the limit values input to control circuitry 184, such as flow rate or pressure-related parameters, may be used to control operation of the pump. Thus, for example, pump 182 may be continuously on until a parameter related to the pressure or flow attains some predetermined value, after which the pump is shut off for several seconds.

It is expected that when implanted in the heart, apparatus 180 will provide short-term retrograde perfusion of the myocardium using the cardiac venous system, and will cause a redistribution of flow within the venous system so that a greater fraction of the deoxygenated blood exits via the lymphatic system and the Thebesian veins. While the venous system is not co-extensive with the coronary arteries (particularly with respect to the right ventricle), it is nevertheless expected that the method and apparatus of the present invention will provide short-term relief and preservation of ischemic myocardium in the majority of cases, since right ventricular infarcts are less common.

As described hereinabove, apparatus 180 may be implanted in a patient suffering from ischemic heart disease to reduce the load on the heart and preserve the myocardium from further infarction pending corrective surgery (i.e., either cardiac bypass surgery, heart replacement, or angioplasty). In addition, in accordance with the methods of the present invention, apparatus 180 may be left in position in the patient during a cardiac bypass operation or angioplasty procedure to preserve the myocardium. Upon completion of the corrective procedure, apparatus 180 then may be advantageously used to reduce the load on the left ventricle during revival of the heart and weaning of the patient from the cardiopulmonary bypass.

In addition to the foregoing uses, apparatus 180 may be advantageously used prior to corrective surgery in a diagnostic role. Specifically, regions of left ventricle dysfunction may be determined by comparing the distribution of nuclear isotopes, such as Technicium and Thallium, when the heart is at rest or stressed, to the distribution of isotopes observed after a period of retroperfusion via the coronary venous system. Such comparisons may yield important information with respect to, for example, how many bypass grafts are required and preferred locations for placement of such grafts, as described in the above-mentioned article to Udelson.

Figure 19:
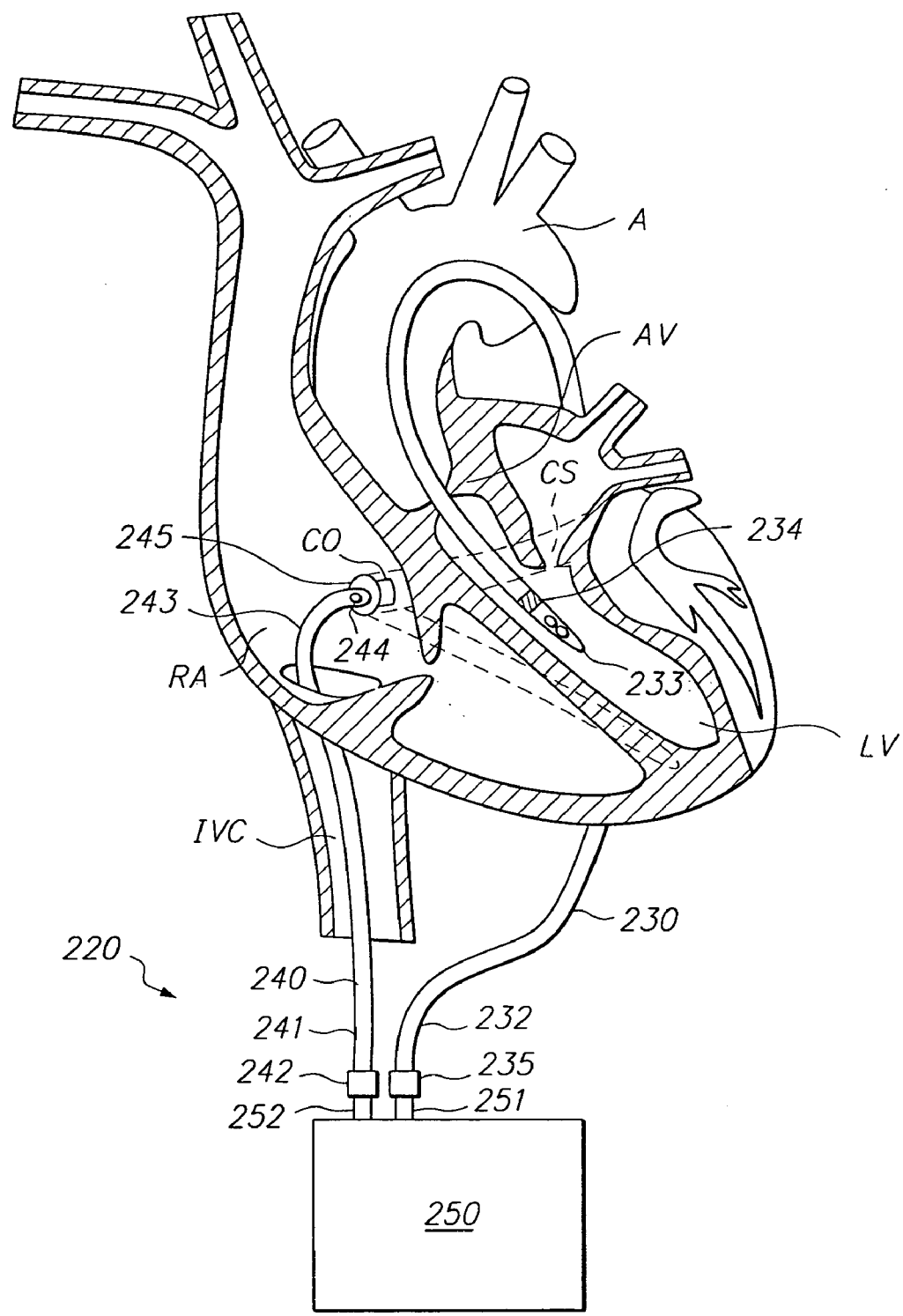
FIG. 19 is a perspective view of a human heart, partly in section, illustrating implantation of a further alternative embodiment of the apparatus of the present invention.

Referring now to FIG. 19, an alternative embodiment of the apparatus of the present invention is described. Apparatus 220 comprises conduit 230, conduit 240 and hydraulically-actuated pump 250. As illustrated in FIG. 19, inlet end 231 of conduit 230 is configured to be inserted via a femoral artery and through aorta A and aortic valve AV into left ventricle LV. Alternatively, inlet end 231 may be placed anywhere in the aorta or femoral artery. Conduit 240 is configured to be inserted via a femoral vein and through inferior vena cava IVC and right atrium RA into the coronary sinus via the coronary ostium CO.

Figure 20:
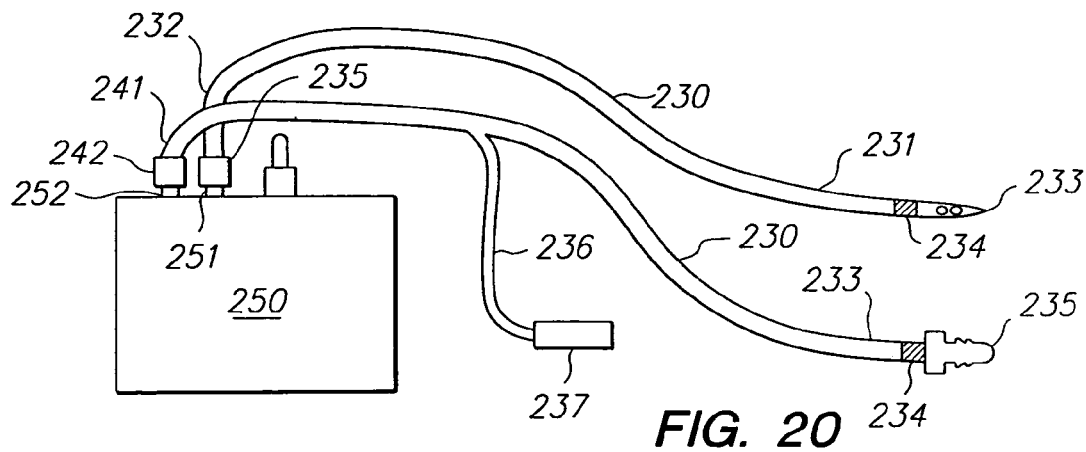
FIG. 20 is a perspective view of the apparatus of FIG. 19.

With respect to FIG. 20, conduit 230 is similar to conduit 190 described hereinabove, and includes inlet end 231, outlet end 232, tapered tip 233, radio-opaque marker band 234 and fitting 235. Conduit 240 is similar to conduit 200 described hereinabove, and includes inlet end 241 having fitting 242 and outlet end 243 having radio-opaque marker band 244 and plug 245 that engages the coronary sinus and partially or fully occludes the coronary ostium. Conduit 240 also may include branch 246 including fitting 247 to permit air to be removed from the fluid circuit, for example, by injecting saline solution.

Pump 250 includes inlet 251 that accepts fitting 235 of outlet end 232 of conduit 230, and an outlet 252 that accepts fitting 242 of inlet end 241 of conduit 240. Pump 250 preferably serves as an accumulator into which a volume of oxygenated blood is pumped by the left ventricle, and includes an hydraulically-actuated mechanism for periodically forcing the accumulated blood into the coronary sinus via conduit 240. Thus, hydraulic energy is transmitted to, and stored in, the mechanism as blood flows into the accumulator, and periodically released to pump blood from the accumulator into conduit 240.

Figure 21A:
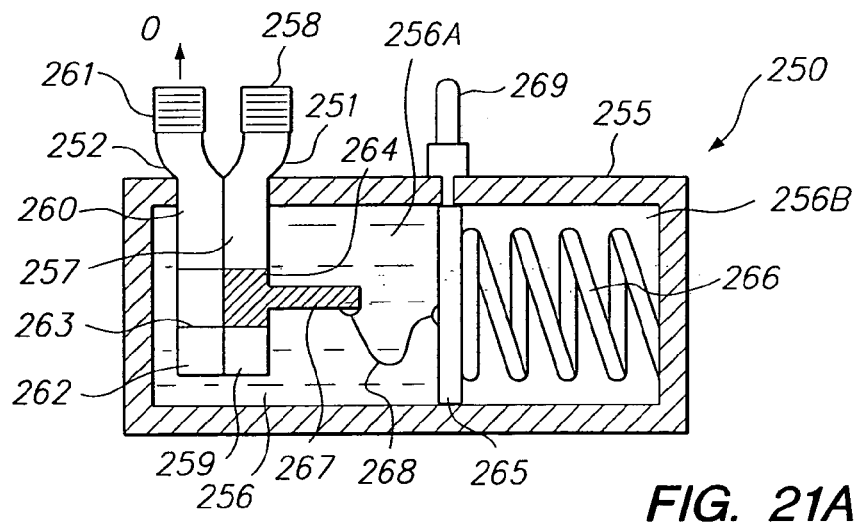
FIGS. 21A and 21B are, respectively, sectional views of the pump portion of the apparatus of FIGS. 19 and 20 in the outflow and inflow states.
Figure 21B:
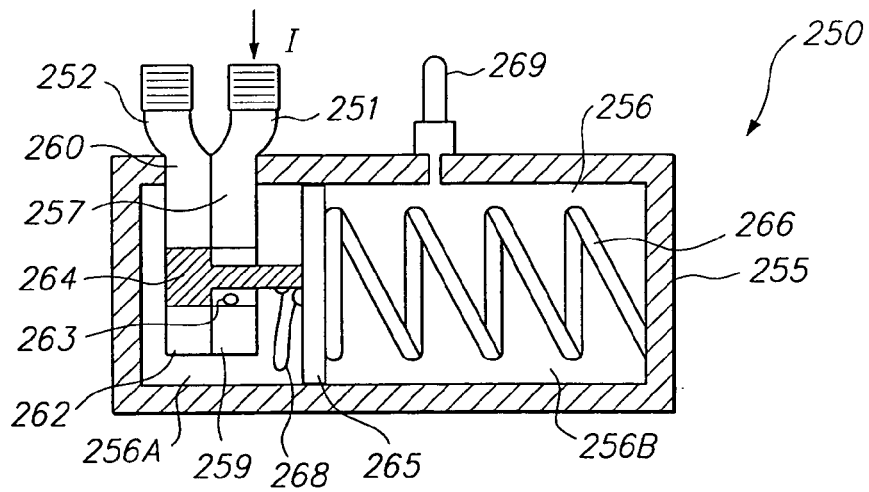

Referring to FIGS. 21A and 21B, a first illustrative embodiment of hydraulically-actuated pump 250 constructed in accordance with the principles of the present invention is described. Pump 250 comprises housing 255 forming chamber 256. Inlet 251 comprises tube 257 having fitting 258 that engages fitting 235 of conduit 230, and outlet 252 that communicates with chamber 256. Outlet 252 comprises tube 260 having fitting 261 that engages fitting 242 of conduit 240, and inlet 262 that communicates with chamber 256. Tubes 257 and 260 are connected by manifold 263 in which valve 264 is reciprocated, as described hereinbelow.

Piston 265 is disposed within housing 255 in contact with spring 266. Piston 265 preferably forms a fluid tight seal that retains fluid in volume 256A of chamber 256, while preventing seepage of fluid into volume 256B containing spring 266. Valve 264 includes rod 267, which is coupled to the face of piston 265 by strand 268. Housing 255 optionally may include cartridge 269 which communicates with volume 256, and dispenses a metered amount of drug or tissue growth agent when chamber 256 is filled and volume 256B is compressed a predetermined degree.

Where the apparatus of FIG. 19 is used to provide retroperfusion during a beating-heart surgical procedure, such as a CABG procedure or angioplasty, housing 255 may be submerged in a cooling bath (not shown), or cartridge 269 may be used to dilute blood passing through chamber 256 with chilled saline. In this manner, a mild degree of hypothermia may be induced in the myocardium to further preserve ischemic regions.

Valve 264 is disposed in manifold 263 so that the valve block inlet 262 of tube 260 when blood is being accumulated in volume 256A of chamber 256, and blocks outlet 259 of tube 257 when piston 265 is ejecting the fluid from within chamber 256 into conduit 240. In FIG. 21A, pump 250 is shown in a state wherein blood (indicated by arrow O) previously accumulated in volume 256A of chamber 256 is being ejected by piston 265. In particular, valve 264 is shown blocking tube 257, and blood in volume 256A is ejected through outlet 252 into conduit 240 by the force exerted by spring 266.

As piston 265 ejects the blood from chamber 256 (e.g., by moving to the left in FIG. 21A), piston 265 contacts rod 267 and moves valve 264 so that it slides from a position blocking inlet 251 (in FIG. 21A) to a position blocking outlet 252 (see FIG. 21B). Once valve 264 closes tube 260 of outlet 252, blood (indicated by arrow I) is pumped into chamber 256A through conduit 230 and outlet 259 by the left ventricle. Blood thereby accumulates in volume 256A, causing spring 266 to become compressed. Cartridge 269, if provided, preferably is configured to inject a metered amount of a drug, e.g., an anti-clotting drug, such a heparin, or a tissue growth agent, such a VEG-F, into volume 256A. When volume 256A becomes full, strand 268 is pulled taut, and causes valve 264 to block outlet 259 of tube 257 and open inlet 262 of tube 260, thus causing valve 264 to return to the position shown in FIG. 21A.

Pump 250 serves as an accumulator to store blood injected into chamber 256 over the course of several heartbeats, and periodically and asynchronously injects the accumulated fluid into the coronary venous vasculature. Volume 256A of pump 250 preferably is from 10 to 100 ml of blood, and spring force 266 is selected to provide a flow rate, during outflow through conduit 240, of between 5–100 ml/sec. It is expected that pump 250 therefore will provide a mechanism to enhance perfusion and washout of metabolites from ischemic myocardium. Pump 250 may be initially filled with saline solution via fitting 237 and branch 236 to flush air out of the system.

Figure 22A:
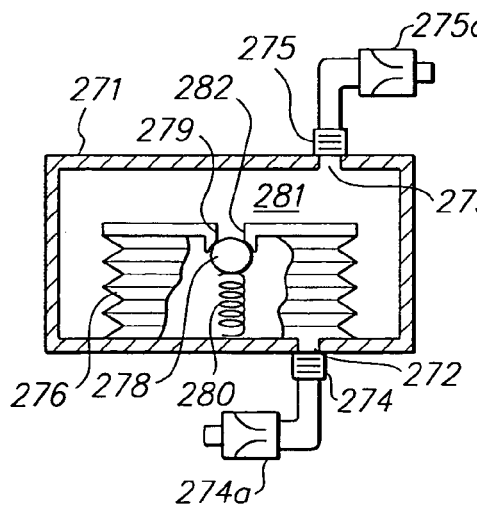
FIGS. 22A and 22B are, respectively, sectional views of an alternative pump portion constructed in accordance with the principles of the present invention.
Figure 22B:
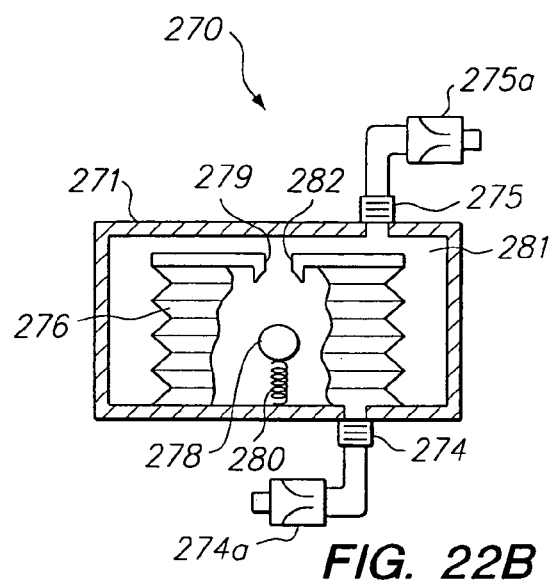

Referring now to FIGS. 22A and 22B, alternative pump 270 constructed in accordance with the principles of the present invention is described. Pump 270, which may be substituted for pump 250 of FIGS. 19 and 20, includes housing 271 having inlet 272 and outlet 273. Inlet 272 includes one-way valve 274a and fitting 274 that engages fitting 235 of conduit 230, while outlet 273 includes fitting 275 that engages fitting 242 of conduit 240 and one-way valve 275a. One-way valve 274a prevents blood injected into bellows 276 during systole from flowing in the reverse direction during diastole.

Inlet 272 opens into bellows 276 (shown partly cut-away), which is biased to maintain a collapsed position. Ball 278 sits in seat 279 and is biased away from seat 279 by spring 280. Housing 271 defines variable size volume 181 (depending upon the extension of bellows 276) that communicates with outlet 273. Bellows 276 includes opening 282 in seat 279 that permits volume 281 to communicate with the interior of the bellows when ball 278 is pulled free of seat 279.

Operation of pump 270 is as follows: during an inflow state, shown in FIG. 22A, blood accumulates within bellows 276, causing blood in volume 281 to be displaced through one-way valve 275a into conduit 240. Ball 278 remains seated in seat 279 against the bias force of spring 280, due to the pressure differential between the interior of bellows 276 and volume 281, which is proportional to that between the left ventricle and the coronary sinus. As bellows 276 fills with blood pumped from the left ventricle via conduit 230, the bellows expands.

At a predetermined degree of expansion of bellows 276, determined by the bias force of spring 280, the force applied by spring 280 overcomes the pressure differential that keeps ball 278 in seat 279. Ball 278 therefore is pulled way from seat 279, as shown in FIG. 22B, allowing bellows 276 to contract, and transferring the blood inside the bellows into volume 281. After bellows 276 contracts a predetermined amount, ball 278 again becomes seated in seat 279, and the above-described cycle of operation is repeated.

Figure 23A:
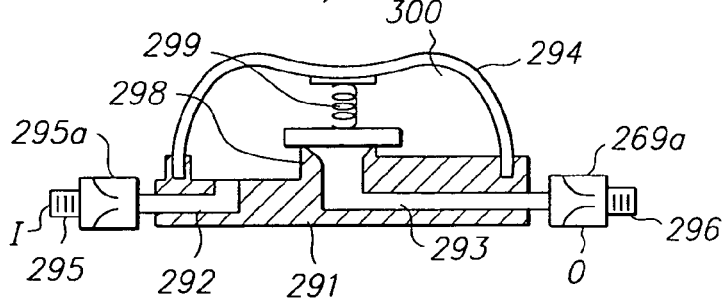
FIGS. 23A and 23B are, respectively, sectional views of a further alternative pump suitable for use in the apparatus of FIGS. 19 and 20.
Figure 23B:
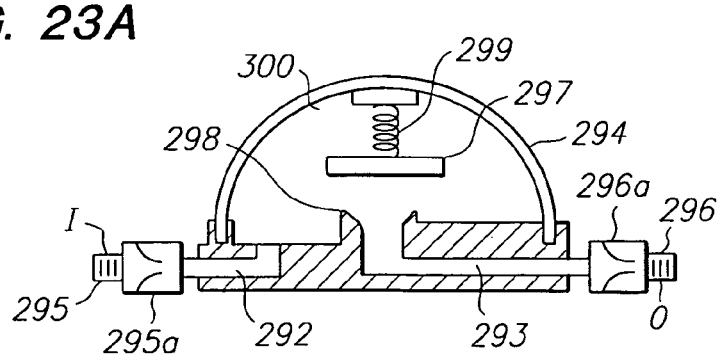

Referring to FIGS. 23A and 23B, a further alternative of an hydraulically-actuated pump constructed in accordance with the present invention is described. Pump 290, which also may be substituted for pump 250 of FIGS. 19 and 20, includes housing 291 having inlet 292, outlet 293 and dome 294. Inlet 292 includes one-way valve 295a and fitting 295 that engages fitting 235 of conduit 230, while outlet 293 includes optional one-way valve 296a and fitting 296 that engages fitting 242 of conduit 240. Dome 294 preferably comprises a compliant material, such as an elastomer, or a metal-alloy having a deflected position in the relaxed state, as shown in FIG. 23A.

Inlet 292 opens into volume 300 defined by dome 294 and an upper surface of housing 291. Poppet 297 is biased against seat 298 by spring 299. Poppet 297 sits atop seat 298, and blocks flow from volume 300 from exiting dome 294 via outlet 293. One-way valve 295a prevents blood injected into dome 294 from returning to the left ventricle during diastole.

Operation of pump 290 is as follows: during an inflow state, shown in FIG. 23A, spring 299 causes poppet 297 to remain seated in seat 298 until blood flowing into the dome through one-way valve 295a causes the dome to expand. As dome 294 fills with blood pumped from the left ventricle via conduit 230, dome 294 either expands radially outward (if a compliant material) or deflects outwardly, as depicted in FIG. 23B. At a predetermined degree of expansion or deflection of dome 294, spring 299 pulls poppet 297 away from seat 298, as shown in FIG. 23B, allowing dome 294 to return to its unexpanded, or undeflected, state. When dome 294 contracts, blood accumulated within volume 300 is ejected through outlet 293, one-way valve 296a, and conduit 240 into the coronary venous vasculature. When dome 294 again contracts a predetermined amount, poppet 297 again contacts seat 298, and the above-described cycle of operation is repeated.

Accordingly, like the embodiments of FIGS. 21 and 22, pump 290 provides a hydraulically actuated device that accumulates blood from the left ventricle, thus reducing the load on the left ventricle, and asynchronously pumps that blood into the coronary venous vasculature to enhance perfusion. Also, like the embodiments of FIGS. 21 and 22, pump 290 requires no external power source, but instead stores hydraulic energy transmitted from the left ventricle over the course of several cardiac cycles in a mechanism that permits that energy to be periodically recovered to infuse blood into the coronary venous vasculature.

While preferred illustrative embodiments of the invention are described above, it will be obvious to one skilled in the art that various changes and modifications may be made therein without departing from the invention and the appended claims are intended to cover all such changes and modifications which fall within the true spirit and scope of the invention.

What is claimed is:

1. An apparatus that is implanted within the chest of a human subject to provide retrograde transvenous myocardial perfusion, the apparatus comprising:
   an inlet conduit having an inlet end, an outlet end and a lumen extending between the inlet end and the outlet end, the inlet end of said inlet conduit being inserted into the aorta or left heart of the subject with the remainder of the inlet conduit extending partially around the subject's heart within the subject's chest cavity such that oxygenated blood enters the inlet end of the inlet conduit and travels through the entire length of the inlet conduit without passing outside of the subject's body;
   an outlet conduit having an inlet end, an outlet end and a lumen extending between the inlet end and the outlet end, the outlet end of the outlet conduit being inserted into the coronary venous circulation of the subject's heart with the remainder of the inlet conduit extending partially around the subject's heart within the subject's chest cavity;
   a coupler positioned within the subject's chest cavity and coupling the outlet end of the inlet conduit to the inlet end of the outlet conduit so that oxygenated blood flows from the outlet end of the inlet conduit, through the coupler, through the entire length of the outlet conduit and into the coronary venous circulation of the subject's heart without passing outside of the subject's body.

2. The apparatus of claim 1 wherein the coupler is disposed on one of the inlet conduit and the outlet conduit.

3. The apparatus of claim 1 wherein the inlet conduit is integrally formed with the outlet
   conduit and the coupler comprises a length of conduit disposed between the inlet conduit and outlet conduit.

4. The apparatus of claim 1 further comprising:
   a sensor coupled in fluid communication to one of the inlet and outlet conduits for monitoring a flow-related parameter.

5. The apparatus of claim 1 further comprising:
   a drug infusion device coupled in fluid communication to the inlet and outlet conduits, the drug infusion device infusing a predetermined amount of a therapeutic agent into blood flowing into the patients coronary venous vasculature via the outlet conduit.

6. The apparatus of claim 5 further comprising:
   means for infusing a predetermined amount of a cooled saline into the volume of blood flowing into the patient's coronary venous vasculature via the outlet conduit.

7. The apparatus of claim 1 further comprising:
   means coupled in fluid communication to the inlet and outlet conduits for monitoring a flow-related parameter for blood flowing into the patient's coronary venous vasculature via the outlet conduit.

8. The apparatus of claim 1 further comprising:
   a drug infusion device for infusing a predetermined amount of a therapeutic agent into blood flowing through the device.

9. The apparatus of claim 1 further comprising a pump coupled between the outlet end of the inlet conduit and the inlet end of the outlet conduit.

10. The apparatus of claim 9 further comprising:
a drug infusion device for infusing a predetermined amount of a therapeutic agent into blood flowing through the device.

11. The apparatus of claim 9 further comprising control circuitry that may be programmed to cause the pump to operate on a predetermined duty cycle.

12. The apparatus of claim 9 wherein the pump comprises a mechanism having a first state wherein the mechanism stores hydraulic energy transmitted by blood entering a portion of the device upstream of the outlet conduit and a second state wherein the mechanism periodically releases the stored energy to pump blood into the outlet conduit.

13. The apparatus of claim 1 wherein the inlet conduit is configured to be placed in a source of oxygenated blood selected from the group consisting of:

the left atrium, left ventricle, aorta, pulmonary vein, subclavian artery, brachiocephalic artery, radial artery or femoral artery.

14. The apparatus of claim 1 wherein the inlet end of the inlet conduit comprises a portion defining a plurality of lateral openings that communicate with the lumen of the inlet conduit.

* * * * *